United States Patent
Peleg

(10) Patent No.: US 10,932,656 B2
(45) Date of Patent: Mar. 2, 2021

(54) SYSTEM AND METHOD FOR SELECTING FOR DISPLAY IMAGES CAPTURED IN VIVO

(71) Applicant: GIVEN IMAGING LTD., Yoqneam (IL)

(72) Inventor: Dori Peleg, Haifa (IL)

(73) Assignee: GIVEN IMAGING LTD., Yoqneam (IL)

(*) Notice: Subject to any disclaimer, the term of this patent is extended or adjusted under 35 U.S.C. 154(b) by 117 days.

(21) Appl. No.: 16/302,130

(22) PCT Filed: May 18, 2017

(86) PCT No.: PCT/IL2017/050559
§ 371 (c)(1),
(2) Date: Nov. 16, 2018

(87) PCT Pub. No.: WO2017/199258
PCT Pub. Date: Nov. 23, 2017

(65) Prior Publication Data
US 2019/0175000 A1 Jun. 13, 2019

Related U.S. Application Data

(60) Provisional application No. 62/338,032, filed on May 18, 2016.

(51) Int. Cl.
*G06T 7/00* (2017.01)
*A61B 1/04* (2006.01)
*A61B 1/00* (2006.01)

(52) U.S. Cl.
CPC ........ *A61B 1/041* (2013.01); *A61B 1/00009* (2013.01); *G06T 7/0014* (2013.01);
(Continued)

(58) Field of Classification Search
CPC ............... G06T 7/0014; G06T 7/0016; G06T 2207/10068; G06T 2207/30096; A61B 1/41; A61B 1/00009
See application file for complete search history.

(56) References Cited

U.S. PATENT DOCUMENTS 8,682,142 B1 * 3/2014 Boskovitz ............ G11B 27/034
386/278
9,342,881 B1 * 5/2016 Peleg .................... G06T 7/0012
(Continued)

*Primary Examiner* — Ping Y Hsieh
(74) *Attorney, Agent, or Firm* — Pearl Cohen Zedek Latzer Baratz LLP

(57) ABSTRACT

A method executed by a system for selecting images from a plurality of image groups originating from a plurality of imagers of an in-vivo device includes calculating, or otherwise associating, a general score (GS) for images of each image group, to indicate the probability that each image includes at least one pathology, dividing each image group into image subgroups, identifying a set Set(i) of maximum general scores (MGSs), a MGS for each image subgroup of each image group; and selecting images for processing by identifying a MGS|max in each set S(i) of MGSs; identifying the greatest MGS|max and selecting the image related to the greatest MGS|max. The method further includes modifying the set Set(i) of MGSs related to the selected image, and repeating the steps described above until a predetermined criterion selected from a group consisting of a number N of images and a score threshold is met.

21 Claims, 12 Drawing Sheets

(52) U.S. Cl.
CPC .. *G06T 7/0016* (2013.01); *G06T 2207/10068* (2013.01); *G06T 2207/30096* (2013.01)

(56) References Cited

U.S. PATENT DOCUMENTS

2009/0043164 A1* 2/2009 Hasegawa .......... A61B 1/00002
    600/118
2009/0309977 A1* 12/2009 Gevrekci ................ H04N 7/15
    348/180

* cited by examiner

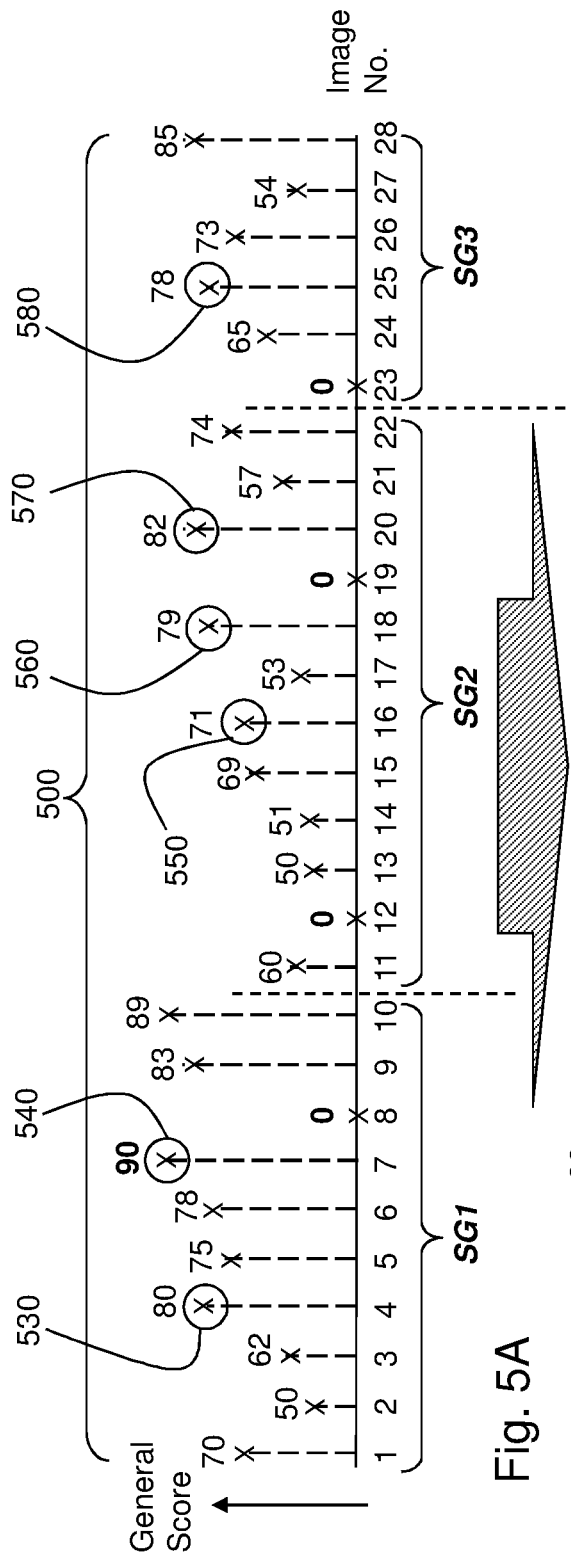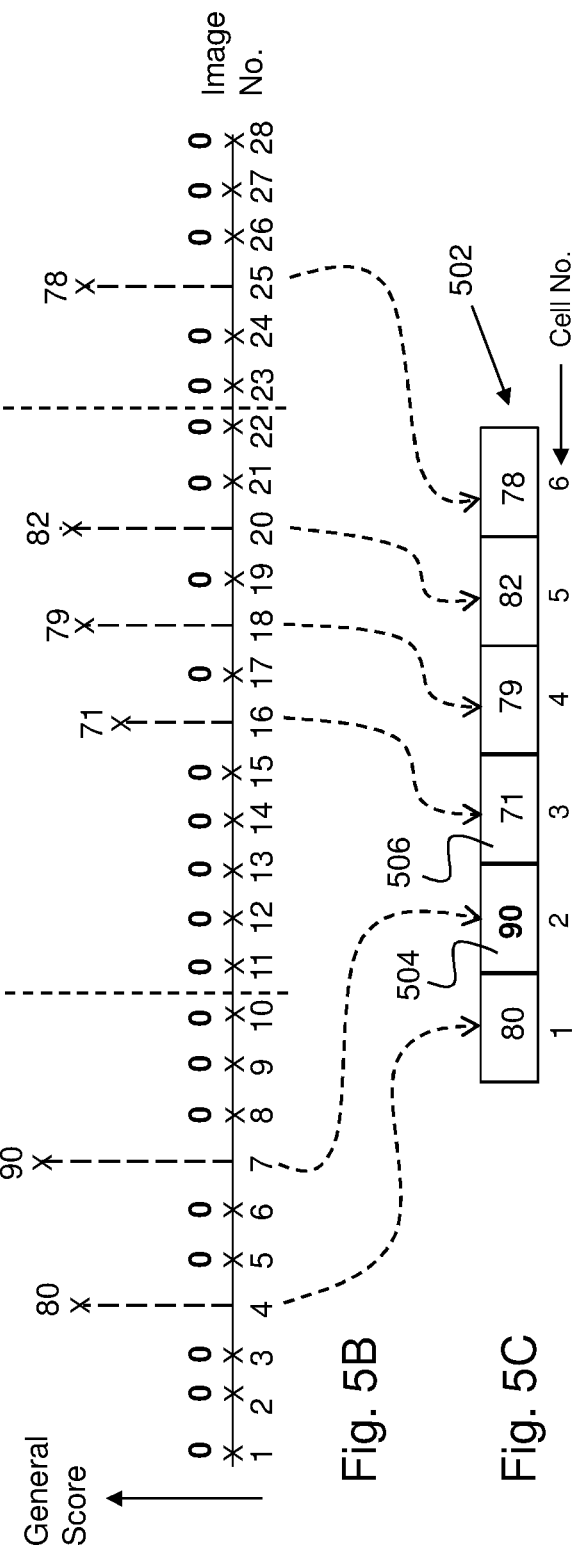
Fig. 5A    Fig. 5B    Fig. 5C

SYSTEM AND METHOD FOR SELECTING FOR DISPLAY IMAGES CAPTURED IN VIVO

CROSS-REFERENCE TO RELATED APPLICATIONS

This application is a National Phase Application of PCT International Application No. PCT/IL2017/050559, International Filing Date May 18, 2017, claiming priority of US Patent Application(s) No(s). 62/338,032, filed May 18, 2016 which is/are hereby incorporated by reference.

FIELD OF THE INVENTION

The present invention relates to a method and system for selecting images for display from a series of images captured in vivo. More specifically, the present invention relates to systems and methods for selecting and displaying a number of images of interest captured in-vivo according to a predefined 'budget' of images set in advance.

BACKGROUND OF THE INVENTION

Capsule endoscopy ("CE") provides thousands, for example 100,000 to 300,000, of images of the GI tract per imaging procedure. Reviewing large numbers of images is time consuming and inefficient, and, in addition, having to review so many images may deter some physicians even from trying to do such image reviews. This is so because, when viewing a movie, for example a moving image stream which may be used for medical diagnosis, a viewer may want to view only certain frames, or may wish to view a short preview only, summarizing only specific frames which are of particular interest (e.g., according to a pre-set criteria), while skipping other images that are unimportant or less important. For example, an in-vivo imager may capture, for example, 150,000 images during a procedure, only some of which may include polyps and/or bleeding sites and/or other pathologies within the gastrointestinal ("GI") tract. For example, polyps, ulcers, diverticulum and bleeding are focal pathologies that can appear only in a few images and, therefore, they might be missed/skipped by the physician if 'hidden' in a very large number of images.

It would be beneficial to highlight to a user, for example a physician, a relatively small set of images that contain the most pathologically conspicuous images, to, thus, save a lot of review time and effort. It would also be beneficial to reduce the number of images, but, at the same time, ensuring that all pathologies in the GI tract, or in a segment thereof, are represented (have at least one representative image) in the smaller set of images.

SUMMARY OF THE INVENTION

In some embodiments, a method for selecting images for processing from images captured by an in-vivo device may include performing, for a group of contiguous images captured in a body lumen (with each image is associated a general score, GS, indicative of a probability that the image includes at least one type of pathology): dividing the group of contiguous images into subgroups of images according to a predetermined criterion (e.g., similarity between whole successive images, a same 'object' appearing in successive images, etc.), selecting an image from a particular image subgroup whose general score, GS, is the greatest in the image subgroup, nullifying the GSs related to the images near the selected image, and repeating the selection and nullification process for the remaining non-nullified GSs until a number N of images is selected, or until the value of an identified greatest GS is lower than a score threshold. (An image subgroup may be formed or created for example by analyzing resemblance between images, and a greatest GS in the subgroup may be identified and its image selected, or a greatest GS may be found, and images may be grouped 'around' the image related to the greatest GS.) Contiguous images may be for example images which are immediately next to each other in a stream when ordered chronologically, for example according to the time of their capture.

In some embodiments, a method for selecting images for processing may include: (i) identifying a greatest GS among the GSs of the images, selecting an image related to the greatest GS and nullifying the greatest GS; (ii) identifying an object in the selected image; (iii) searching for the object which is the same as the identified object in images near the selected image; and (iv) nullifying the GSs related to the images near the selected image, and repeating or iterating steps (i)-(iv) for all the non-nullified GSs until a number N of images is selected, or until the value of an identified greatest GS is lower than a score threshold.

In these embodiments the object in the selected image may be selected from the group consisting of: (1) an entire image, in which case it may be determined (e.g., by a processor) that a selected image and images near the selected image make up an image subgroup if there is similarity (resemblance) between these images, and (2) an imaged object (e.g., pathology), in which case it may be determined (e.g., by a processor) that a selected image and images near the selected image make up an image subgroup if these images include, for example, a same or identical imaged object (e.g., a same pathology, for example a same polyp). In these embodiments, the step of searching for the same object in images near the selected image may include tracking the object backward (in images preceding the currently selected image) and forward (in images subsequent to the currently selected image). In one embodiment 'backward' (and preceding) and 'forward' (and subsequent) refer to the order of images in the portion of image stream making up the group of contiguous images based on, for example, time of capture of an image or other ordering. Thus 'backward' may be, for example, looking to images before the current image in time, or time of capture, or ordering in an image stream, and forward may be the reverse.

In some embodiments a method applied to a group of contiguous images captured in a body lumen by using one imager, where each image may be associated with a general score ("GS") indicative of a probability that the image includes at least one type of pathology, and a distance, d, indicative of a distance between images, may include: dividing, or separating, the group of contiguous images, or a portion thereof, into image subgroups, where each image subgroup includes a base image and images resembling to the base image; identifying a maximum general score ("MGS") for each image subgroup, and selecting images for processing, the selecting may include: (i) identifying the greatest MGS (MGS|max) in the MGSs identified for the image subgroups and selecting the image related to or having the greatest MGS; (ii) nullifying the MGS related to or having the selected image; (iii) modifying each MGS based on a distance d between an image related to or having the particular MGS and each selected image; (iv) identifying, in the modified MGSs, a modified MGS which has the maximum value (MGS|max). Embodiments may further include selecting the image that is related to or having that modified MGS; and repeating steps (ii)-(iv) until a predetermined criterion selected from a group consisting of a number N of images and a score threshold is met. The N selected images, or a subset of the N selected images, may be, for example, displayed on a display device for a user. The MGS in each image subgroup may be a local maxima general score in the image subgroup.

Modifying each particular GS (e.g., MGS) may be based on a distance, d, between the image related to, or having, the particular GS (or MGS) and a nearest selected image. Modifying the particular GS (or MGS) may be performed by identifying a minimum distance, Dmin, between the image related to or having the particular GS (or MGS) and any of the selected images, and modifying the particular GS (or MGS) using the minimum distance, Dmin. (The smaller Dmin, the greater a reduction in the value of the particular GS or MGS.) The distance, d, between an image related to or having a GS (or MGS) and a selected image may be calculated or measured in units of: (i) time, or (ii) a number of intervening images, or (iii) a number of intervening image subgroups, or (iv) a distance that the in-vivo device traveled in the body lumen while taking the images, or (v) a distance that the in-vivo device traveled in the body lumen with respect to a landmark in the group of images or in the body lumen. Each unit instance may be calculated or measured as: (i) an absolute value calculated or measured relative to a beginning of the group of contiguous images, or relative to a beginning of the body lumen, or relative to a landmark in the group of contiguous images or in the body lumen, or as (ii) a percentage or fraction of the group of contiguous images or body lumen, or (iii) a percentage or fraction of a video clip including all, or most of, the group of contiguous images, or (iv) a percentage or fraction of a distance traveled by the in-vivo device, or (v) a percentage or fraction of a time traveled by the in-vivo device.

Modifying GSs (e.g., MGSs) may include applying a modification function to the GS or MGSs with respect to a selected image. The modification function may be selected from a group consisting of: symmetrical function, asymmetrical function, linear function, non-linear, Gaussian exponent, exponent with an absolute value of distance, a step function, and a triangularly shaped function with its apex located at a selected frame and linearly decreases with distance. The modification function may be selected according to a parameter selected from a group consisting of: type of pathology, location in the GI tract and velocity of the in-vive device in the body lumen.

Embodiments may include applying a modification function to GSs or MGSs based on a location in the body lumen at which the images related to the MGSs were captured. The body lumen may be the gastrointestinal tract, and a first modification function may be applied to GSs or MGSs related to images captured in the small bowel, and a second modification function may be applied to GSs or MGSs related to images captured in the colon.

Embodiments may include zeroing out (e.g., setting to zero) a general score of an image if the image is noisy. The image may be regarded as noisy if it contains bubbles and/or gastric content and/or if the image provides tissue coverage below a tissue coverage threshold value and/or the image complies with a darkness criterion.

An image general score may be calculated by using a number m of score values, S1, . . . , Sm, respectively outputted by m pathology detectors, the m score values indicating probabilities that the image includes m, or k (k<m), types of pathologies. A pathology may be selected from the group consisting of: a polyp, a bleeding, a diverticulum, an ulcer, a lesion and a red pathology.

In other embodiments a method applied to q groups of contiguous images respectively captured in a body lumen by q imagers, with each image of each group are associated a general score (GS) indicative of a probability that the image includes at least one type of pathology, and a distance, d, indicative of a distance between images of the respective group, may include: for each image group of the q groups of contiguous images, performing: (A) dividing, or separating, the image group, or a portion thereof, into image subgroups, each image subgroup comprising a base image and images resembling to the base image, and (B) identifying a set Set(i) (i=1, 2, 3, . . . ) of maximum general scores (MGSs), the set Set(i) of maximum general scores comprising a maximum general score (MGS) for each image subgroup of the image group; and selecting images for processing by performing: (i) identifying a maximum MGS (MGS|max) in each set S(i) of MGSs; (ii) identifying, among all the MGSs|max, the greatest MGS|max, and selecting the image related to the greatest MGS|max; (iii) nullifying the greatest MGS|max related to the selected image; (iv) modifying the particular set Set(i) of MGSs related to the selected image based on a distance d between images respectively related to the MGSs of the particular set Set(i) of MGSs and each selected image; and repeating steps (i)-(iv) until a predetermined criterion selected from a group consisting of a number N of images and a score threshold is met.

The in-vivo device may include a number of imagers selected from one and two, and modifying a particular set Set(i) of MGSs related to a selected image originating from a first imager may include modifying MGSs of the particular set Set(i) also based on images originating from the second imager.

A system for selecting images from images captured by a number q of imagers of an in-vivo device may include a storage unit for storing q groups of contiguous images respectively captured in a body lumen by q imagers, and for storing, in association with each image of each group, a general score (GS) indicative of a probability that the image includes at least one type of pathology, and a distance, d, indicative of a distance between images of the respective group, and a data processor. The data processor may be configured to, for each image group of the q groups of contiguous images: (A) divide, or separate, the image group, or a portion thereof, into image subgroups, each image subgroup comprising a base image and images resembling to the base image, and (B) identify a set Set(i) (i=1, 2, 3, . . . ) of maximum general scores (MGSs), the set Set(i) of maximum general scores may include a maximum general score (MGS) for each image subgroup of the image group. The data processor may be also configured to select images for processing by: (i) identifying a maximum MGS (MGS|max) in each set S(i) of MGSs; (ii) identifying, among all the maximum MGSs, the greatest MGS|max, and selecting the image related to the greatest MGS|max; (iii) nullifying the greatest MGS|max related to the selected image, and (iv) modifying the particular set Set(i) of MGSs related to the selected image based on a distance d between images respectively related to the MGSs of the particular set Set(i) of MGSs and each selected image, and to repeat steps (i)-(iv) until a predetermined criterion selected from a group consisting of a number of N images and a score threshold is met.

BRIEF DESCRIPTION OF THE DRAWINGS

The principles and operation of the system and method according to the present invention may be better understood with reference to the drawings, and the following description, it being understood that these drawings are given for illustrative purposes only and are not meant to be limiting, wherein:

FIGS. 5A-5F demonstrate a scores modification process according to an example embodiment of the invention;

Figure 1:
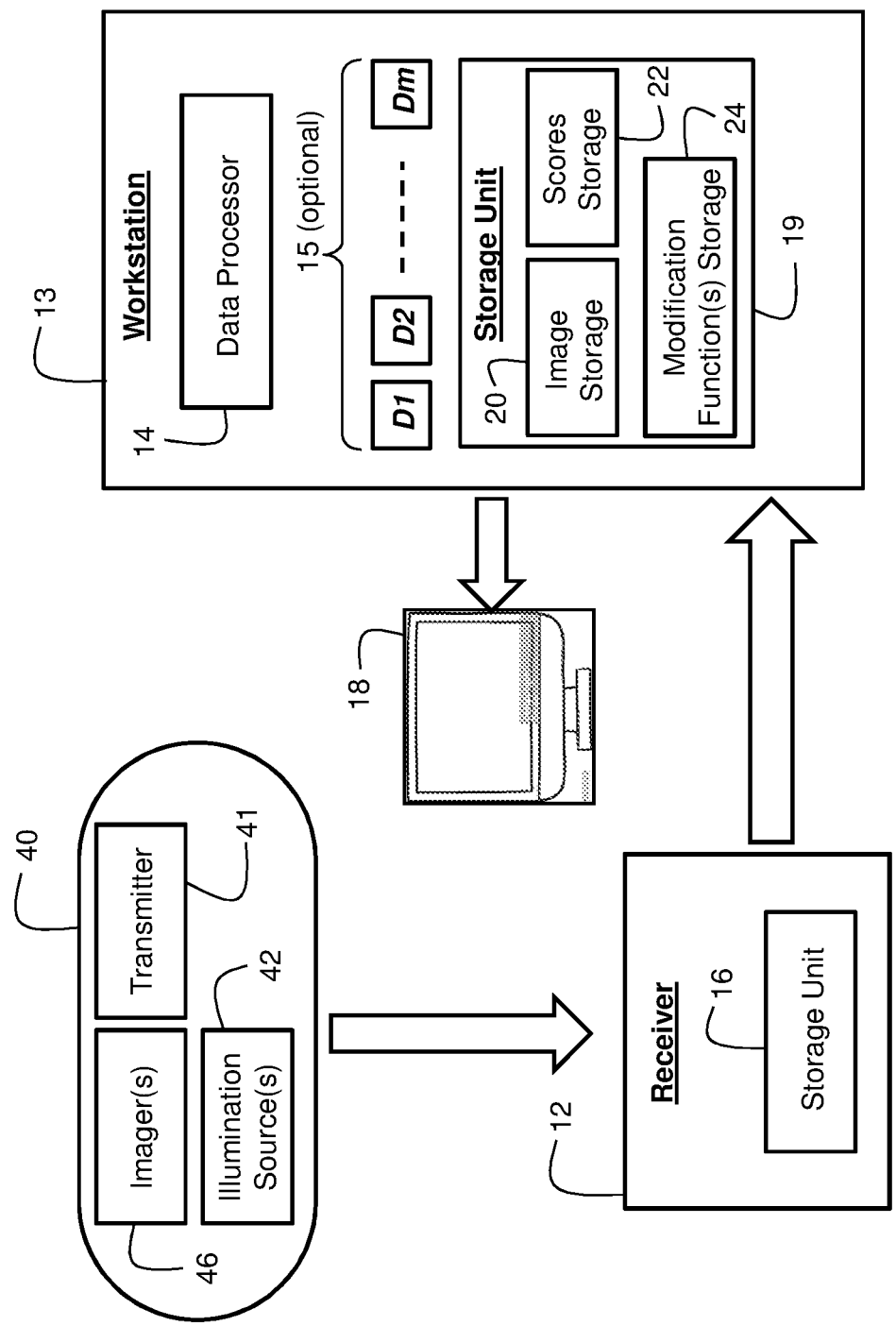
FIG. 1 shows an in-vivo imaging system according to an embodiment of the present invention.

It will be appreciated that for simplicity and clarity of illustration, elements shown in the figures have not necessarily been drawn to scale. For example, the dimensions and/or aspect ratio of some of the elements may be exaggerated relative to other elements for clarity. Further, where considered appropriate, reference numerals may be repeated among the figures to indicate the same, corresponding or analogous elements.

DETAILED DESCRIPTION OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Discussions utilizing terms such as, for example, "processing." "computing." "calculating." "determining," "establishing". "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium that may store instructions to perform operations and/or processes.

Unless explicitly stated, the operations described herein are not subjected to a particular order or sequence. For example, some method steps can occur or be performed simultaneously, at the same point in time, or concurrently, and some method steps can occur or be performed in reversed order.

Embodiments of the systems and methods of the present invention may be used in conjunction with an imaging system or device capable of obtaining images of in-vivo objects. Any imaging device or system that can be incorporated into an in-vivo device may be used, and embodiments of the invention are not limited by the type, nature or other aspects of the imaging system, device or unit used. Some embodiments of the present invention are directed to a swallowable in-vivo device, such as an autonomous swallowable capsule. However, the in-vivo device need not be swallowable or autonomous, and may have other shapes or configurations.

An in-vivo imaging device may capture a series of images as it traverses the GI system, and transmit images, typically by transmitting one image frame at a time. The images may be later compiled at or by a receiver to produce a displayable video clip or an image stream, or a series of images. An image transmitted by the in-vivo imaging device to the receiver may be a color image. In one example, each image may include 256 rows of 256 pixels each, where each pixel may be represented, or has associated therewith, binary data (e.g., bytes) that may represent, for example, the pixel's color and brightness.

Detection of an anomaly in a tissue imaged by an imaging device may include measuring one or more pixel parameters (e.g., color parameter) of one or more pixels in an image. An anomaly detected for display may be any anomaly. e.g., a polyp, a lesion, a tumor, an ulcer, a blood spot, an angiodysplasia, a cyst, a choristoma, a hamartoma, a tissue malformation, a nodule, to list some anomalies.

Embodiments of the present invention are directed to methods and processes for selecting, for example for further processing and/or for analysis and/or for display, a set of relatively small number, N. of images (e.g., 100 images), which is referred to herein as an 'image budget' or limit, such that each image in the group of selected images includes or represents at least one pathology, and the probability that the group of selected images would include multiple images of a same pathology would be minimized in order not to waste the image budget on similar or redundant images. In some embodiments of the present invention, the selected images may be displayed to a user 'as is' (e.g., without further processing). In some other embodiments of the present invention, a selected image may be further processed, where the processing, or further processing, of the selected image may include analysis of the selected image, for example to further investigate the pathology with more robust software tools, for example to corroborate or to refute the initial determination that the image includes the pathology, or to assess the severity of the pathology. A selected image, in conjunction with other, non-selected, images belonging to the same subgroup as the selected image, may be used in the preparation of three-dimensional presentation of the pathology. Further processing of a selected image may include emphasizing a particular area in the image in a way suitable for the pathology, or pathologies, identified in the image, for example to emphasize a pathology, so that the viewer can see it instantly, without having to waste time on searching for it everywhere in the image.

Embodiments of the methods and process for selecting the images may include a phase of applying one or more pathology detectors (D1, D2, . . . , ) to images in order to score them in terms of the probability that they include one or more pathologies, and another phase that includes iteratively or repeatedly selecting images for display, one image at a time, using an 'image budget', or a pathology related score threshold, or a combination of the image budget and the pathology related score threshold, or any other suitable criterion. Using pathology detectors may be optional, as pathology scores may be calculated by some other system (e.g., by a remote computer), and the system and methods subject of the present invention may receive scores from the other system as input and perform the image selection methods based on the received scores. Each time an image is selected for display or for further processing (for example), image scores are modified ('suppressed', reduced in value) in a way that increases the probability that other images that also include clinically important information, though of other pathologies or in other locations or parts in the body lumen, would also be selected for display. 'Suppressing a score' means herein reducing the value of the score by an amount calculated by using a score modification function.

Some embodiments disclosed in the present invention are beneficial to GI imaging because for example they present to a user (e.g., a physician) a small number of images that includes only images which are the most clinically important. In addition, some embodiments disclosed herein enable the user (e.g., the physician) to select any number of important images the user may want to review (e.g., 20 images, or 50 images, etc.), or to apply the image selection process to a particular type of pathology (e.g., polyps), or to a particular location in the GI tract (e.g., colon) while limiting the total number of images including the particular pathology, or including all pathologies in the particular location, to a 'reasonable' or 'convenient' number. That is, instead of having to review thousands of images indiscriminately, a user may use embodiments disclosed herein to review as many images as s/he wants, with each image showing a pathology, and to direct the image selection process to any desired pathology and/or to any desired segment or part of the GI tract. Therefore, embodiments disclosed herein may give a user (e.g., physician) flexibility, for example, in terms of: (1) setting the number of images to be displayed, or further processed, to a desired value, (2) selecting the type of pathology or pathologies that the selected images will show, and (3) selecting the location, or locations, in the GI tract from which images will be selected for display, or for further processing.

The term "object", as used herein, may refer, in some embodiments, to an entire image, for example it may refer to image characteristics, or to image features, that characterize an image as a whole. In other embodiments the term "object" may refer, for example, to an imaged object (that is, an object whose image appears in an image). An imaged object may be, but not limited to, for example, a polyp, a lesion, a bleeding site, a diverticulum, an ulcer, a pathology, etc.

An imaged object (e.g., a polyp) that is contained in a selected image may be small, medium or large relative to the size of the image, and it may be located anywhere in the image and have any angle of rotation with respect to the image. If the imaged object contained in the selected image (the 'original' object) is also contained (also shown) in a near image, a processor may determine (e.g., by using any suitable object characterization algorithm) that the imaged object in the near image and the original object in the selected image are the same or identical imaged object even though the size and/or location and/or the angle of rotation of the imaged object contained in the near image are respectively different than the size and/or location and/or the angle of rotation of the original object. That is, two images may be regarded as similar by or because of their imaged object even though an imaged object in one image is translated or rotated, or has a different size, with respect to the imaged object in the other image.

The term "image subgroup", or "subgroup" for short, as used herein, refers, in some embodiments, to a collection of near images that, together with a related selected image, make up or form a group due to their image characteristics being similar and, therefore, these images may resemble each other through "similarity". In other embodiments the term "subgroup" refers to a collection of near images that make up or form a group due to their including a same imaged object (or a same 'object', for short). Accordingly, after an image is selected (by using any image selection method that is described herein), an image subgroup may be defined, according to some embodiments, with respect to the selected image, by searching for, and finding, near or nearby images that are similar to the selected image (e.g., that have similar image characteristics as the selected image), or, in other embodiments, by searching for, and finding, near or nearby images that include a same (imaged) object as the (imaged) object included in the selected image.

That is, if a selected image contains an object (e.g., a polyp), this object is 'tracked' back, in images preceding the selected image, and forward, in images subsequent to the selected image. The same specific object (e.g., a particular polyp) that is found in a selected image may be found in one or more preceding images and/or in one or more subsequent images, or it may appear (be contained in) only the selected image. (An image subgroup may include only one image; e.g., the selected image.)

FIG. 1 shows a block diagram of an in-vivo imaging system according to one embodiment of the present invention. The system may include an in-vivo imaging device (e.g., imaging capsule) 40. Device 40 may be implemented using a swallowable capsule, but other sorts of devices or suitable implementations may be used. Device 40 may include one or more imagers 46 (e.g., two imagers—one on each side of device 40) for capturing images in a body lumen (e.g., in the GI tract). Device 40 may also include an illumination source (or sources) 42 for illuminating a body lumen, for example in the GI tract of a subject, and a transmitter/receiver 41 for transmitting images (e.g., in the form of data frames) captured in vive by imager(s) 46. Device 40 may also include an optical system including, for example, lenses, to focus reflected light onto imager(s) 46.

Preferably, located outside the patient's body in one or more locations is a receiver 12 to receive, for example, images that device 40 transmits. Receiver 12 may include an antenna or an antenna array that may releasably be attached to the patient. Receiver 12 may include a storage unit 16 (e.g., a computer memory, or a hard disk drive) for storing, for example, all or selected images that receiver 12 receives from device 40. Receiver 12 may also store metadata related to images that it receives from device 40, such as, for example, time information sent by device 40 and indicates the time at which device 40 captures each image and/or the time each image is received at receiver 12. (As described below, for example in connection with FIG. 6C, such time information may be used by a processor to determine (e.g., calculate), in this example temporal, distances between images as prerequisite to modification (suppression) of image general scores.) Preferably, receiver 12 is small and portable, and is wearable on the patient's body during receiving (and recording) of the images.

The in-vivo device system may also include a workstation 13 to which receiver 12 may transfer the images originating from device 40. Workstation 13 may include, or be connected to, an image display device 18 for displaying, among other things, images originating from device 40. Workstation 13 may receive image data, and optionally other type of data, from receiver 12, and process the image data in order to automatically display, for example on display device 18, images (and/or a video clip including a series of images) that were captured by device 40. Workstation 13 may enable a user (e.g., a physician) to, for example, select images for display, or to enhance displayed images. Workstation 13 may enable the user, for example by mouse-clicking, pressing or tapping a button, to commence the image selection process disclosed herein, such that a relatively small, predetermined or configurable, number, N, of images (for example N=100 images) showing (containing) the most clinically important or conspicuous images would be automatically displayed on display device 18 for the physician, rather than expecting the physician to review hundreds or thousands of images, trying to find the important images on her/his own. Workstation 13 may enable the user to select the value of N. Workstation 13 may enable the user to limit the image selection process to a particular part of the body lumen; namely, to select only images that are captured in a particular part of the body lumen, for example in a particular part of the GI tract (e.g., in the small bowel). In some embodiments, the number (N) of selected images is not set in advance but rather, is determined as, or derivable from, a result of using another criterion. For example, a scoring threshold mechanism may be used in the selection of images, as described, for example, in connection with FIG. 7, which is described below. In some embodiments, the number (N) of selected images and a scoring threshold value or mechanism may be used in combination. For example, a scoring threshold value or mechanism may be used as a 'main' criteria, and the number N may be used as a high limit to the number of images that are ultimately selected.

Workstation 13 may include a storage unit 19 and a data processor 14. Storage unit 19 may store q groups of contiguous images respectively captured in a body lumen by q imagers (46). Storage unit 19 may also store, in association with each image of each group, a general score (GS) that indicates a probability that the image includes at least one type of pathology, and a distance, d, that indicates a distance between images of the respective group.

Storage unit 19 may include an image storage 20 for storing image data, a scores storage 22 for storing pathology scores and general scores calculated for images, and a modification function storage 24 for storing one or more modification functions for modifying scores. Scores storage 22 may also store modified scores (scores modified by the modification function(s)). Workstation 13 may include a number m of pathology detectors 15 (e.g., designated as D1, D2, . . . , Dm, to respectively detect m different, like or similar pathologies/anomalies (e.g., focal pathologies). A pathology detector Di (i=1, 2, . . . , m), which may be or include, for example, a pattern recognition classifier, applied to image data may output a (pathology) score representing the probability that the image includes (shows) a pathology of a respective type. The m pathology detectors (15) may not be required because the image pathology scores calculated for images may be calculated elsewhere (e.g., by a remote computer) and be transferred, for example, to workstation 13. A pathology detector may analyze various parameters and/or features in or associated with an image (e.g., intensity level of pixels, color tones, amplifier gain, light exposure time, etc.), and identify features representative or characteristic to the pathology type involved, and, using these features, a classifier, which may be part of the pathology detector, may output a value (e.g., score) indicating the probability that the image includes the pathology.

An image general score may be calculated by using a number m of score values, S1, . . . , Sm, respectively outputted by m pathology detectors, where the m score values indicate probabilities that the image includes m, or k (k<m), types of pathologies. A pathology may be a polyp, a bleeding, a diverticulum, an ulcer, a lesion, a red pathology, etc. (Other pathology types may be detected or identified in images and similarly handled.) An image may include more than one pathology.

Data processor 14 may be configured to carry out embodiments of the invention for example by executing software or code stored for example in storage 19. In some embodiments, detectors 15 or other classifiers, modules, etc. described herein may be, or may be carried out, by data processor 14 executing such code.

In some embodiments, data processor 14 may apply different modification functions to pathology scores related to images that were captured in different parts of the body lumen. For example, modification, or suppression, of pathology scores related to images that are captured in a first location in the body lumen (e.g., small bowel) may be performed by using a first modification function, while modification of pathology scores related to images that are captured in a second location in the body lumen (e.g., colon) may be performed by using a second modification function, and so on. Data processor 14 may enable a user (e.g., a physician) to select a modification function according to the part of the body lumen from which images were taken, and this may be beneficial because, this way, the user may 'shift the focus' to (that is, bias the image selection process towards) a particular part of the body lumen the user is more interested in. Shifting the focus to (that is, biasing the image selection process towards) a particular part of, or area in, the body lumen may be implemented by, for example, reducing the values of the pathology scores related to the focused on lumen part leniently, while rigorously reducing the values of the pathology scores related to other parts of the lumen.

Data processor 14 may process the image data stored in image storage 20, and, in some embodiments, use the m detectors to calculate, for each image, various types of pathology scores. Processor 14 may store the various scores in score storage 22, and update, from time to time, the scores content of score storage 22. Updating the scores in score storage 22 by processor 14 may include, for example, adding new scores, zeroing scores, scaling scores and updating scores by using the modification function(s) that are stored in modification function storage 24. Processor 14 may use the scores calculation and modification (suppression) process to select, for example for display, a predetermined number, N, of the most clinically important images captured by in-vivo device 40. Processor 14 may iteratively or repeatedly select one such image at a time, and every time processor 14 selects an image, processor 14 may store, for example in image storage 20, the selected image, or a reference information (e.g., a pointer) that references the selected image. The way processor 14 calculates and modifies, or suppresses, pathology scores and use them to select the N clinically most important images is described and exemplified hereinafter.

By way of example, data processor 14 may be configured, among other things, to perform as described below for each image group of the q groups of contiguous images: (A) Divide. or separate, the image group, or a portion thereof, into image subgroups, each image subgroup comprising a base image and images resembling to the base image, and (B) Identify a set Set(i) (i=1, 2, 3, . . . ) of maximum general scores (MGSs), the set Set(i) of maximum general scores comprising a maximum general score (MGS) for each image subgroup of the image group; and to select images for processing by: (i) identifying a maximum MGS (MGS|max) in each set S(i) of MGSs; (ii) identifying, among all the maximum MGSs, the greatest MGS|max, and selecting the image related to the greatest MGS|max; (iii) nullifying the greatest MGS|max related to the selected image; and (iv) modifying the particular set Set(i) of MGSs related to the selected image based on a distance d between images respectively related to or having the MGSs of the particular set Set(i) of MGSs and each selected image. Data processor 14 may repeat steps (i)-(iv) until a predetermined number N of images has been selected for display or for further processing, or until the value of an identified (modified) maximum MGS (MGS|max) is lower than a score threshold, Sth.

Data processor 14 may be or include any standard data processor, such as a microprocessor, multiprocessor, accelerator board, or any other serial or parallel high performance data processor. Display device 18 may be a computer screen, a conventional video display, or any other device capable of providing image and/or other data.

Preferably, imager 46 may be or include a CMOS camera or another device, for example, a CCD camera. Illumination source 42 may include, for example, one or more light emitting diodes (LEDs), or another suitable light source.

During operation, imager 46 captures images and sends data representing the images to transmitter 41, which transmits images to receiver 12 using, for example, electromagnetic radio waves. Receiver 12 transfers the image data to work station 13 for storage, processing and displaying. The in-vivo imager may capture a series of still images as it traverses the GI tract. The images may be later presented by workstation 13 as, for example, a stream of images or a video clip of the traverse of the GI tract. The in-vivo imaging system may collect a large volume of data, as the device 40 may take several hours to traverse the GI tract, and may record images at a rate of, for example, two images every second, or twenty four images every second, etc., resulting in the recordation of thousands of images. The image capturing and transmission rate (or frame capture rate, or 'frames per second' rate) may vary.

Preferably, the image data recorded and transmitted by device 40 is digital color image data, although other image formats may be used. By way of example, each image frame includes 256 rows of 256 pixels each, each pixel including, or represented by, digital bytes whose values represent, for example, color and brightness, according to known methods.

Figure 2:
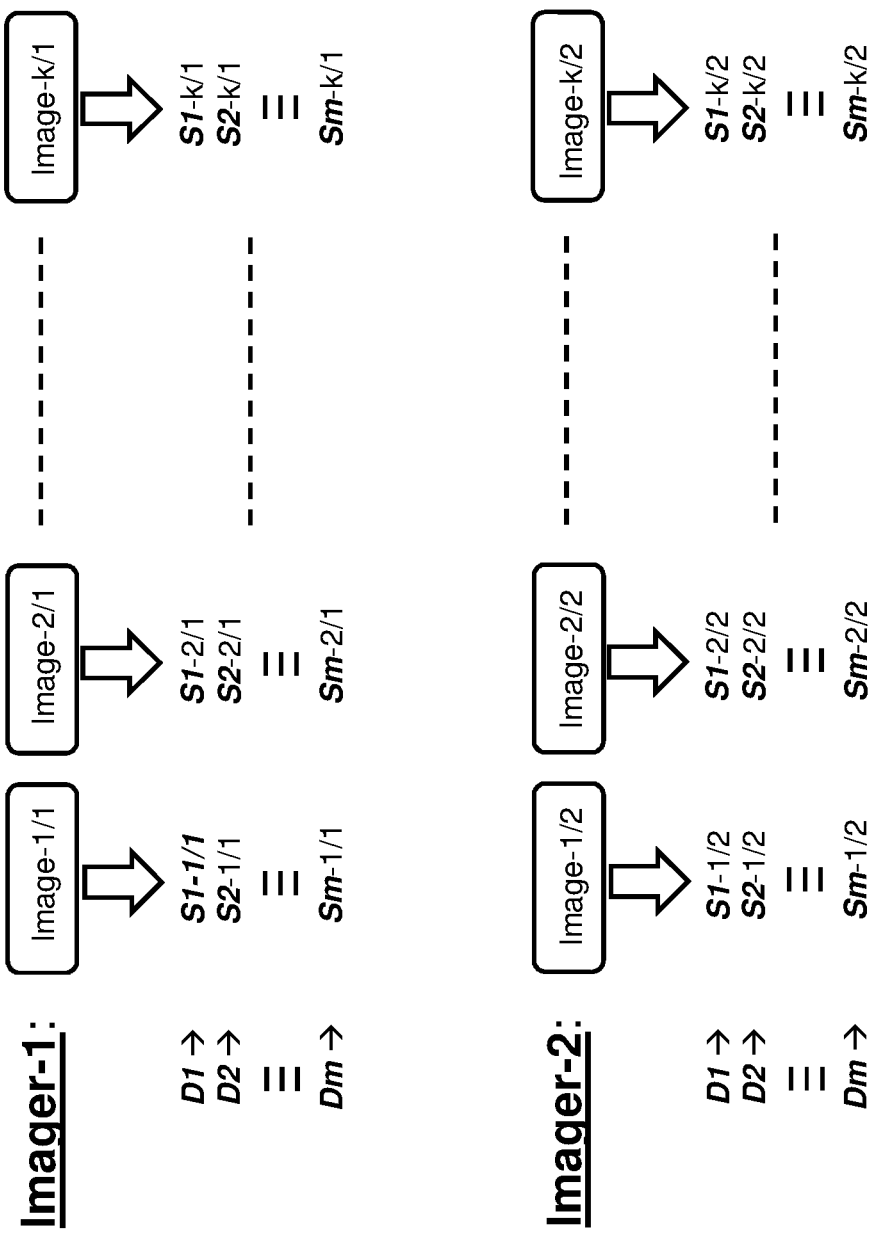
FIG. 2 diagrammatically illustrates an image scoring scheme according to an embodiment of the present invention.

FIG. 2 schematically illustrates an image scoring scheme according to an embodiment of the present invention. FIG. 2 is described in association with FIG. 1. Assume that in-vivo device 40 includes two imagers ("Imager-1" and "Imager-2"), and each imager captured a number k of images by the time device 40 was excreted by the patient. (Embodiments described herein may likewise be applicable to any sequence of images, regardless of the number of imagers involved in their capturing. For example, embodiments described herein may likewise be applicable to a sequence of images that were captured by an in-vivo device including one imager.) Also assume that each image is analyzed using a number m of pathology detectors, where each detector is configured to detect a different, or similar, pathology in images by calculating a score, Si, for each image such that a score calculated for a particular image indicates the probability that a GI site captured by the particular image includes the particular pathology. By way of example, a first pathology detector may be configured to detect polyps in the colon; a second pathology detector may be configured to detect bleeding in the GI tract; a third pathology detector may be configured to detect ulcers in the GI tract; a fourth pathology detector may be configured to detect diverticulum in the GI tract, etc. Alternative or additional pathology detectors may be used. A particular pathology may be detected by using more than one detector. For example, one polyp detector may detect a polyp by detecting its contour line, another polyp detector may detect a polyp by detecting colors patterns characterizing polyps, etc.

Referring to FIG. 2, Imager-1 captured a group of k contiguous images, designated as Image-1/1 (image #1 of imager-1), Image-2/1 (image #2 of imager-1), . . . , Image-k/1 (image #k of imager-1). Similarly, Imager-2 captured a group of k contiguous images, designated as Image-1/2 (image #1 of imager-2), Image-2/2 (image #2 of imager-2), . . . , Image-k/2 (image #k of imager-2). Images that are contiguous may be, for example, images that are immediately precedent or subsequent to each other in an image stream.

Applying m detectors to Image-1/1 results in m scores (a score per detector), designated as S1-1/1 (detector 1's score calculated for image 1 of Imager-1), S2-1/1 (detector 2's score calculated for image 1 of Imager-1), . . . , Sm-1/1 (detector m's score calculated for image 1 of Imager-1). Similarly, applying the m detectors to Image-2/1 results in m scores (a score per detector), designated as S1-2/1 (detector 1's score calculated for image 1 of Imager-1), S2-2/1 (detector 2's score calculated for image 1 of Imager-1), . . . , Sm-2/1 (detector m's score calculated for image 1 of Imager-1), and so on.

Similarly, applying the m detectors to Image-1/2 results in m scores (a score per detector), designated as S1-1/2 (detector 1's score calculated for image 1 of Imager-2), S2-1/2 (detector 2's score calculated for image 1 of Imager-2), . . . , Sm-1/2 (detector m's score calculated for image 1 of Imager-2). Similarly, applying the m detectors to Image-2/2 results in m scores (a score per detector), designated as S1-2/2 (detector 1's score calculated for image 2 of Imager-2). S2-212 (detector 2's score calculated for image 2 of Imager-2), . . . , Sm-2/2 (detector m's score calculated for image 2 of Imager-2), and so on. Each image may, therefore, have associated with it m scores that respectively indicate probabilities that the image includes (images) various pathologies.

Figure 3:
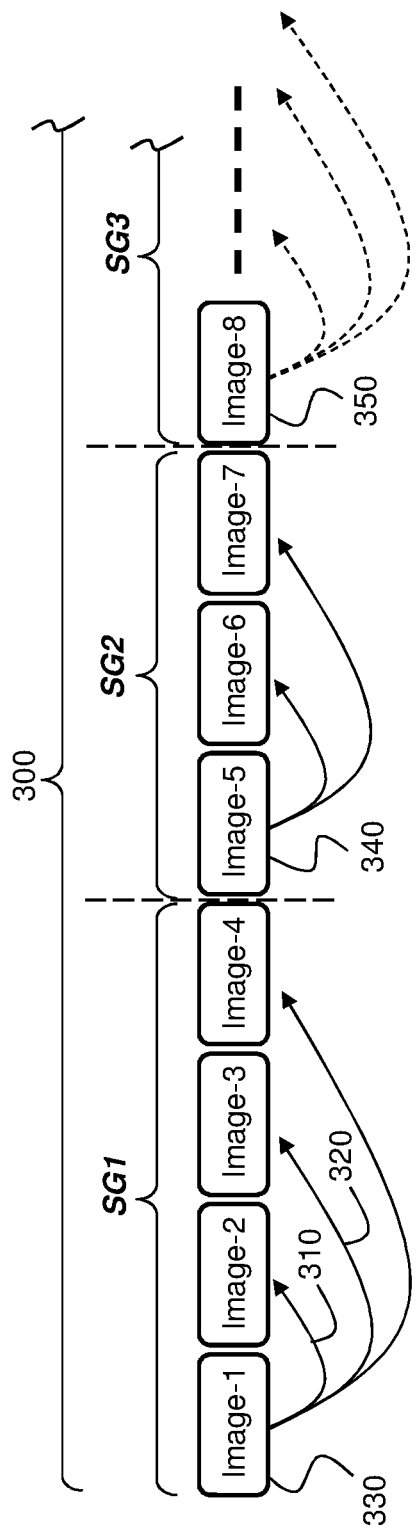
FIG. 3 diagrammatically illustrates an image grouping scheme according to an embodiment of the present invention.

FIG. 3 schematically illustrates an example of image grouping according to an embodiment of the present invention. For the sake of simplicity, FIG. 3 shows a group 300 of contiguous images captured by one imager.

An image subgroup (SGi) includes temporally successive images that resemble each other or are similar to each other (e.g., in terms of visual features; e.g., configurative features, or computed features; e.g., ratio between image parameters, for example light intensities, color levels, etc.), and, therefore, they may show or include a same pathology (e.g., polyp, bleeding, ulcer, lesion, diverticulum, etc.). However, since the image 'budget' (e.g., the limit or maximum number. N) of images to be selected for display (for example) is very small (comparing to the total number of thousands or tens of thousands of captured images), images that are similar to each other within a same image subgroup can be detracted or removed from further processing (e.g., detracted or removed from the image selection process), leaving only a representative image from each image subgroup that represents the respective image subgroup.

To start grouping images (to start partitioning the image group) into subgroups, a similarity level is checked (310) between a first image, designated as 'Image-1', and a temporally contiguous image, designated as 'Image-2'. In the example of FIG. 3, Image-1 and Image-2 are assumed to be similar. Similarly, similarity between Image-1 and Image-3 is checked (320). In the example of FIG. 3. Image-1 and Image-3 are also assumed to be similar. Similarly, similarity between Image-1 and Image-4 is checked. In the example of FIG. 3 Image-1 and Image-4 are also assumed to be similar. Similarly, similarity between Image-1 and Image-5 is checked. In the example of FIG. 3, Image-1 and Image-5 are dissimilar. Therefore, continuing the example, the first image subgroup (SG1) includes four images: Image-1 (image 330, which may be regarded as a base image of image subgroup SG1), Image-2, Image-3 and Image-4. The same image grouping process continues for the next image subgroups (SG2) by using image Image-5 (image 340) as a new subgroup's base image. Image 340 is the first image that does not belong to image subgroup SG1 due to it being dissimilar to the base image 330 of image subgroup SG1. Therefore, image 340 is used as a base image of image subgroup SG2, and, by way of example, subgroup SG2 includes three images: Image-5. Image-6 and Image-7. Image subgroup SG3 includes image Image-8 as its base image (350), and additional images that are not shown in FIG. 3. Additional image subgroups may be identified in a similar way. Similarity between images may be determined (for example calculated) based on any suitable criteria, or by using other image grouping methods. For example, similarity between images may be determined based on comparison of preselected features or parameters (e.g., light intensity, color(s), etc.), or similarity between images may be determined in a reversed order, or "backwards"; that is, from a particular image to previously captured images. Images may be grouped using any suitable clustering method.

An image group may be partitioned using other methods. For example, an image group may be partitioned into image subgroups such that each image subgroup has the same number of images. In some embodiments, the number of images of, or included in, an image subgroup may depend on the part or organ of the body lumen (e.g., in the small bowel, or in the colon) the in-vivo device captures the images. To this effect, a location of the in-vivo device in the body lumen may be detected from, or determined based on, for example, one or more images, or by using an external localization system. Then, or concurrently, the location of the in-vivo device may be transferred to, for example, workstation 13 (FIG. 1), and stored, for example, in storage unit 19, in association with the image, or images, that was/were captured in this location. By way of example, data processor 14 may partition or divide images captured in the small bowel into small image subgroups, and images captured in the colon into large image subgroups, or vice versa. (A 'small image subgroup' includes a smaller number of images comparing to the number of images of a 'large image subgroup'.)

Figure 4A:
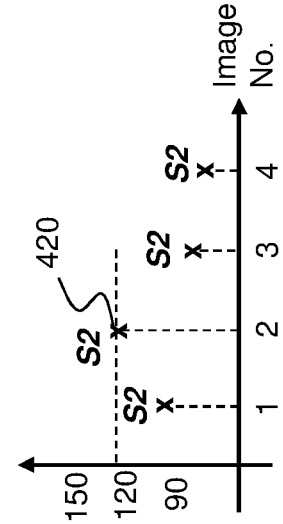
FIGS. 4A and 4B show example scoring graphs according to an embodiment of the present invention.
Figure 4B:
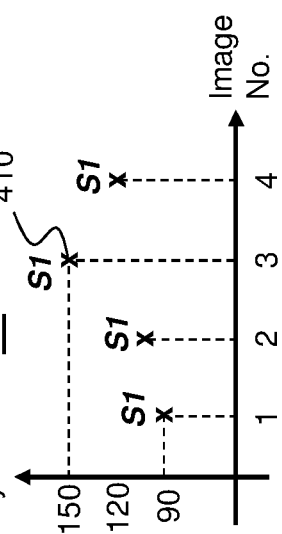

FIGS. 4A and 4B show example scoring graphs according to an embodiment of the present invention. FIG. 4A and FIG. 4B are described in association with FIG. 3, and they respectively show example scores that are calculated for image subgroup SG1 by applying two pathology detectors—D1 and D2—on each image of subgroup SG1. (As described herein, for example in connection with FIG. 1 and FIG. 2, a number m of detectors (D1, D2, . . . , Dm) may be applied to each image of an image group in order to calculate, for the image, a number m of scores (S1, S2, . . . , Sm) that respectively indicate the probability that the image shows, or include, m pathologies of the types respectively detectable by the m detectors.)

FIG. 4A shows example scores (S1s) obtained for image subgroup SG1 by using pathology detector D1. By way of example, image subgroup SG1 includes four images which are designated in FIG. 4A as '1', '2'. '3' and '4' on the "Image No." axis. (The same image numbers are also used in FIG. 4B.) For example, assume that the scores calculated by detector D1 for the four images are: S1=90 for image No. 1, S1=105 for image No. 2. S1=150 for image No. 3, and S1=124 for image No. 4. FIG. 4B shows example scores (S2s) obtained for subgroup SG1 by applying pathology detector D2. For example, assume that the scores calculated by detector D1 for the four images are: S2=95 for image No. 1, S2=125 for image No. 2, S2=80 for image No. 3, and S2=75 for image No. 4.

After the various scores (e.g., one score per detector per image) are calculated for each image of each of image subgroups SG1. SG2, SG3, and so on, local maxima score values are identified for each score type and for each image subgroup. By way of example, score value S1=150, shown at 410 (FIG. 4A), is the local maximum of the scores calculated by pathology detector D1 for image subgroup SG1, and score value S2=125, shown at 420 (FIG. 4B), is the local maximum of the scores calculated by pathology detector D2 for image subgroup SG1. An image subgroup may include more than one local maxima score value for a particular pathology detector, and different pathology detectors may produce different numbers of local maxima score values for a same image subgroup.

Figure 4C:
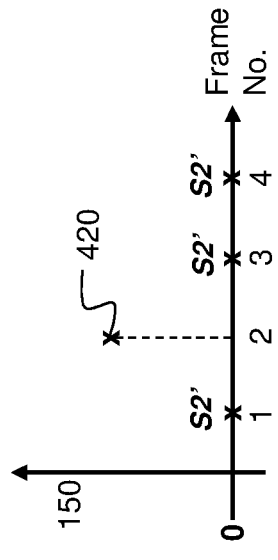
FIG. 4C and FIG. 4D respectively show manipulation of scoring in the scoring graphs of FIG. 4A and FIG. 4B according to an embodiment of the present invention.
Figure 4D:
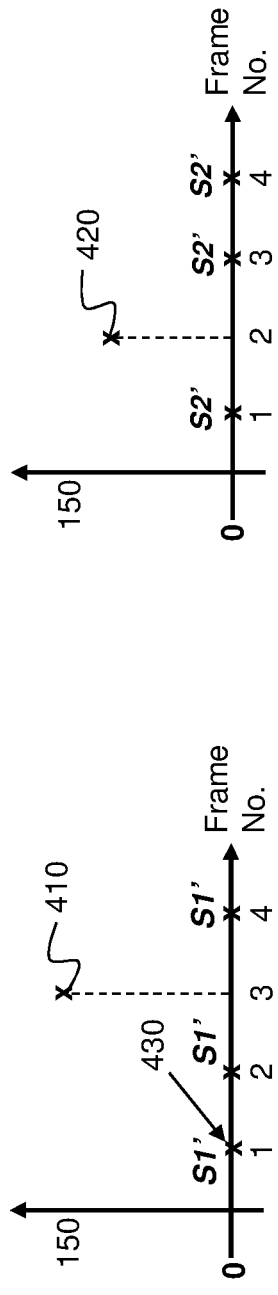

The local maxima score values identified in each image subgroup may be processed further in the image selecting process, whereas the other scores (scores which are 'non-conspicuous' scores) may be excluded from this process. Exclusion of 'non-conspicuous' scores (scores that are not local maximum scores) may be implemented by, for example, zeroing them out, or by reducing their value to an arbitrary value that is lower than the lowest pre-suppressed score value, in order to ensure their exclusion from the selection process. Score values S1s and S2s in FIGS. 4A-4B that are zeroed out are shown in FIGS. 4C-4D as S1's and S2's. For example, the zeroed out version of score value S1 related to image No. 1 is shown in FIG. 4C, as S1' (at 430). (In the example shown in FIGS. 4A-4D score values S1's related to images '1', '2' and '4'—see FIG. 4C—and score values S2's related to images '1', '3' and '4'—see FIG. 4D—are zeroed out). Non-conspicuous scores may be excluded from the image selection process because they may represent images that may be less clinically important (in terms of the pathology associated with the type of these scores) than the images having the local maximum score values. In some embodiments, one image may be selected from an image subgroup even though other images in the image subgroup may be as clinically important as the selected image. After the non-conspicuous score values related to all score types and images are zeroed out, a general image score may be calculated for images by using the local maxima score values. (A zeroed-out score value has no weight in determining an image's general score value.)

By way of example, each of FIGS. 4A-4B shows an image subgroup that includes only a few images and only one local maxima score value for each type of score. However, this is only an example—an image subgroup may include many images (the number of which depends on a similarity degree between images), and, in addition, several local maxima score values. After all local maxima score values are identified in each image subgroup, the non-maxima score values (the other score values) in each image subgroup are zeroed out, as exemplified by FIGS. 4C-4D, which are described below, in order to exclude the images producing (associated with) them from the images' selection process. As described herein, images of an image subgroup are characterized by having a high degree of similarity (for example, above a predetermined similarity threshold value), so, only the more conspicuous images may be selected for display while many other images in each image subgroup can be removed from the images' selection process, for potentially being unimportant or redundant, without risking losing clinically important images. Since all original images are saved (e.g., in image storage 20. FIG. 1), if a particular image is ultimately selected (and, for example, displayed; e.g., to a user), the system (e.g., workstation 13, FIG. 1) may enable the user to display also images that precede or follow that image (e.g., images whose score has been zeroed out). Embodiments of the invention may enable the user to use a selected image (for example when the selected image is displayed) to display the related image subgroup in its entirety, or partly, for example by clicking or tapping the selected image while it is displayed.

Calculating a General Score (GS) for an Image

If all scores of a particular image are zero, meaning that none of the pathology detectors D1, D2, . . . , Dm detected any pathology in that image, the image is categorically excluded from the images' selection process. However, since these detectors (e.g., classifiers) calculate probabilities (that pathologies exist), it is likely that the detectors would output, in such cases, some low, non-zero, score values. In other words, a pathology detector may output a low, non-zero, score value for an image even if the image does not include the pathology. In addition, an image may have more than one low, non-zero, score values (a score value per pathology detector). However, as described herein, if a particular pathology score that is output by a respective pathology detector for a particular image is not a local maxima score value within the image subgroup that includes the particular image, the particular pathology score is zeroed out; e.g., set to zero. Zeroing out all score values that are not local maxima score values in some embodiments guarantees that only the local maxima score values are factored in in the image selection process described herein, as they are more likely to indicate pathologies.

If an image has one local maxima score value, the local maxima score value may be used further as the image's general score (GS) associated with the image. However, as described herein, images may have or be associated with more than one local maxima score value. (Some images may have at least one local maxima score value for more than one pathology detector.) Therefore, a general score, GS, may be derived for and associated with each image from (e.g., calculated based on) all the local maxima score values calculated for, or associated with, the image. An image general (pathology) score, GS, may be calculated, for example, using formula (1) or formula (2):

$$GS = f(S1, S2, \ldots, Sm) \quad (1)$$

$$GS = \text{Max}\{f(S1), f(S2), \ldots, f(Sm)\} \quad (2)$$

where Si (i=1, 2, . . . , m) is a score value output from pathology detector number i, and pathology score values S1, S2, . . . , Sm are pathology scores respectively related to m types of pathologies. Each of pathology score values S1, S2, . . . , Sm may have a value that is either zero (after undergoing the zeroing out process, or without that process) or a local maxima score value. For example, if m=3 (if images are analyzed using three pathology detectors), an image general score, GS, may be calculated using, for example, formula (3):

$$GS = \text{Max}\{W1 \times S1, W2 \times S2, W3 \times S3\} \quad (3)$$

where S1, S2 and S3 are pathology scores respectively related to three pathology detectors, and W1, W2 and W3 are 'weights' respectively related to the three types of pathologies.

An image may have more than one non-zero pathology score, the various scores being associated with more than one type of pathology. In such a case, the image may include a 'dominant' pathology, namely, a pathology that is visually, or otherwise, more conspicuous than the other pathologies included in that image. Therefore, given a stringent image budget, only the clinically most significant images, which are usually images with the highest pathology scores, are selected for display. (Selection of an image may be performed regardless of which type of pathology in the image has the highest pathology score.) Therefore, each image is given or associated with a general pathology score (GS) that represents, or is more 'biased' towards, the more visually, or otherwise, a conspicuous pathology, in order to increase the probability that the image would be selected for display. (Formulas (1)-(3) may be devised to obtain that goal.) It may not matter whether a particular image is selected for display because it has a higher pathology score for some pathology comparing to a pathology score for some other pathology, because, once selected for display, the image would show every pathology that is included in that image, not only the pathology having the highest pathology score.

In some embodiments, knowing the type of the pathology score (knowing the pathology type) that is the reason for the selection of an image may be utilized to enhance the displayed image (e.g., highlight the pathology). For example, if an image is selected for display because it includes a focal pathology (e.g., a polyp), enhancing the image display may include, for example, identifying a polyp's center and overlaying a visually conspicuous cross ('x') on the polyp's center and/or overlaying a visually conspicuous circle (e.g., red circle) around the polyp in order to draw the viewer's (e.g., physician's) attention to the polyp, rather than having the viewer spending time searching for it in the image. In another example, if an image is selected for display because it includes a fragmented or distributed pathology, enhancing the image may include overlaying a visually conspicuous boundary line (e.g., a circle, a box, etc.) on the fragmented/distributed pathology, or highlighting the whole image without committing to the exact location of the pathology in the image, in order to draw the attention of the viewer (e.g., physician) to the pathology, rather than having the viewer spending time searching for it in the image.

Figure 5D:
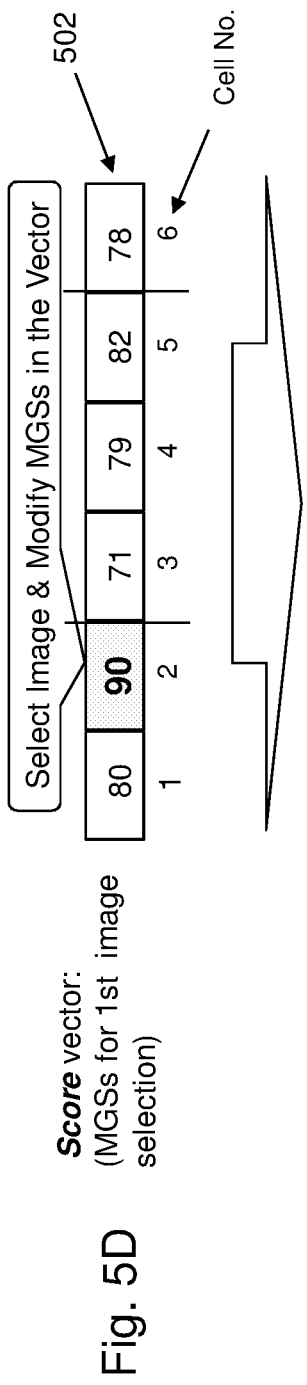

FIGS. 5A-5E demonstrate an image selection process according to an example embodiment. FIG. 5A shows an example image group 500 including twenty eight contiguous images captured by an in-vivo device including one imager, and their respective general scores. (The twenty eight images are shown ordered temporally, according to the time of their capture, with image number '1' captured first and image number '28' captured last.) In practice, the number of images in an image group may be very large (e.g., tens of thousands), however the small number of images shown in FIG. 5A is used only for illustrative purpose. FIG. 5A also shows image group 500 partitioned into three image subgroups (SGs), designated as SG1, SG2 and SG3. Images of an image group may be captured at a rate that may be as low as, for example, two images per second, or at a much higher rate, for example, 74 images per second. The images selection methods disclosed herein are not limited to, or by, any particular image capturing rate; the image selection methods disclosed herein are applicable to any image capturing rate.

Assume that the images of image group 500 were analyzed by two pathology detectors (e.g., polyp detector and bleeding detector), and that a general (pathology) score, GS, was calculated for each image using any of formulae (1)-(3) based on the pertinent two scores output by the two pathology detectors. Also assume that filtering detectors (e.g., content detector, bubble detector, tissue coverage detector, etc.) were used to detect images that show, for example, content and/or bubbles, etc., in some site(s) of the GI tract, and assume that such images are assigned a score value zero (cf. image numbers 8, 12, 19 and 23 in FIG. 5A) in order to exclude them from the image selection process.

After image group 500 is processed in the way described herein, for example, in connection with FIG. 3 and FIGS. 4A-4D, the images are partitioned or divided, or separated, in this example, to three image subgroups SG1. SG2 and SG3 based on similarity between images. (For the sake of simplicity, image group 500 includes twenty eight images and three image subgroups, and the images budget (the number of images to select, for example, for further analysis and/or display), is three.)

After the images are partitioned or divided, or separated, to image subgroups, all local maxima general score (MGSs) values may be identified in each image subgroup. (The MGSs are shown circled in FIG. 5A.) For example, there are two MGS values in image subgroup SG1 (MGS values 80 and 90, which are respectively shown at 530 and 540, are respectively related to images 4 and 7), three MGS values in image subgroup SG2 (MGS values 71, 79 and 82, which are respectively shown at 550, 560 and 570, are respectively related to images 16, 18 and 20), and one MGS value in image subgroup SG3 (MGS value 78, which is shown at 580, is related to image 25).

In some embodiments, every MGS in every image subgroup may be used (participate) in the image selection process, while the other score values may be 'suppressed' by, for example, zeroing out; e.g., setting to zero, their value. In FIG. 5B, every MGS in each of image subgroups SG1 to SG3 is used in the image selection process, while the values of the other (non-local maxima) scores of FIG. 5A are zeroed out. In other embodiments, only the MGS having the greatest value among the MGSs in each image subgroup is used in the image selecting process, whereas the other scores (other MGSs and the non-local maxima score values alike) are zeroed out.

FIG. 5C shows a score vector 502 that includes every MGS of each image subgroup: the two MGSs that are related to image subgroup SG1, the three MGSs that are related to image subgroup SG2, and the one MGS that is related to image subgroup SG3. (By 'vector' is meant herein an ordered set of values.) The score vector may include only MGSs that are the greatest in the respective image subgroups, for example only MGS=90 from image subgroup SG1, only MGS=82 from image subgroup SG2 and the one MGS (MGS=78) from image subgroup SG3.) Score vector 502 may also include, or has associated with its MGSs content, information regarding the relative location of the images (for example in the image group 500) that are related to (that resulted in) the MGSs that are stored in score vector 502. (Each image location may be associated with the related MGS.) By way of example, the two MGS values 90 and 71 (shown at 504 and 506, respectively) are adjacent in score vector 502. However, distances between MGSs do not necessarily translate into distances between the images related to these MGSs. For example, while two MGSs may be adjacent in score vector 502, their related images may be far from each other (e.g., a large number, e.g., 35, of images may intervene (e.g. be located in-between in an ordered image stream) between the images related to these MGSs). So, with each MGS may be associated location information that may: (1) indicate a location of the related image, and (2) enable to calculate a distance, d, which may be measured; e.g., as time (e.g., as differences between image capturing times), as intervening images, or other measures of distance between any two images. An image subgroup may include, have associated with it or results in more than one maximum (pathology) score, as each pathology detector may produce one maximum score for each image subgroup. In some embodiments, if an image subgroup has two or more maximum scores, only the highest maximum score (that is, only the maximum score having the highest value among the two or more maximum scores) is used as an image general score (GS) in the image selection process. This way, only one image can be selected from each image subgroup. For example, (referring again to FIGS. 4A-4B), the image subgroup SG1 includes two maximum scores—maximum score 410 and maximum score 420, and only maximum score 410 may be selected for the image selection process, due to its value (150) being higher than the value (~125) of maximum score 420.

In some embodiments, score vector 502 may have a length (in terms of the number of the vector elements) corresponding to the number of images in the image group. (Score vector 502 may contain a score value for each image in the image group, though some score values may be local maxima score values while other score values may be zero, for example as a result of the score values zeroing out process described herein and exemplified, for example, in FIG. 5B, or if the images related to these score values were detected as including, for example, content or bubbles, or as not showing enough tissue, etc.)

In some embodiments, score vector 502 may contain all the MGSs identified in each image subgroup, or only the greatest MGS from each image subgroup. Since MGSs may be identified one MGS at a time, the length of scores vector 502 may change (lengthened) by one vector element each time a new MGS is identified in each image subgroup. (Depending on the value of the pathology score(s) calculated by the pathology detector(s) for each image, an image subgroup may include one MGS or multiple MGSs.)

With each MGS that is added to score vector 502 may be associated location information regarding the location of the related image relative to the locations of the other images in the image group, or relative to a reference point. The reference point may be, for example, temporal (e.g., capture time of a particular image), or a physical landmark in or related to a body lumen from which the images are taken. A location of an image relative to the location of other images may be determined (e.g., calculated) based on, for example, the time each image is captured, or based on a serial number of the orderly captured images, where the first image that is captured may be assigned serial number one (for example), the second image that is captured may be assigned serial number two, and so on. (Other image discrimination schemes may be used.)

The relative location of images in the image group may be used, as described herein, to determine (e.g., calculate) distances between images (e.g., in terms of time differences, in terms of the number of intervening images, etc.). Distances between images are used, as described herein, to variably (e.g., in de-escalating way) modify (suppress) MGSs in order to reduce the chance that images near an already selected image would be selected for display (for example), and, at the same time, to somewhat increase the chance that 'remote' images (relative to the selected image) would still be selected even though their original score values (MGSs) may be relatively low. (The term 'remote' is used herein in relation to an already selected image.)

After an image is selected (for example for further analysis and/or for display), the MGSs of the other images may be variably modified, or suppressed, such that the farther an image is from a selected image, the more moderately its score value is lowered (suppressed), hence the de-escalating nature of the score values modification process with respect to each selected image. While a distance between an image related to a particular MGS and some selected image may be relatively long, a distance between the image related to the particular MGS and another selected image (if more than one image have already been selected) may be shorter. In such a case, the particular MGS may be modified rigorously using the shorter distance, rather than modifying, or suppressing, it moderately using the longer distance, the reason for this being that it may be desired to lower the chance that the image related to the particular MGS (which the shorter distance, Dmin, suggests that it resembles to the nearest selected image) would be selected.

Figure 5E:
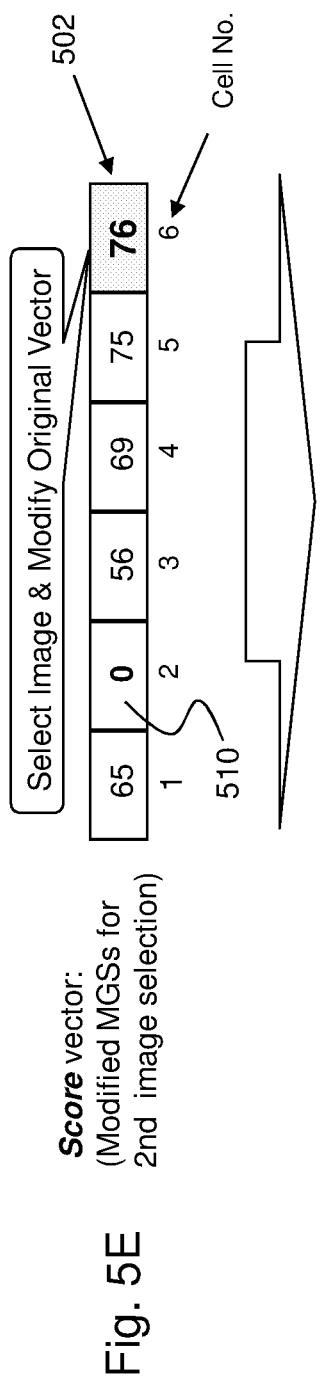
Figure 5F:
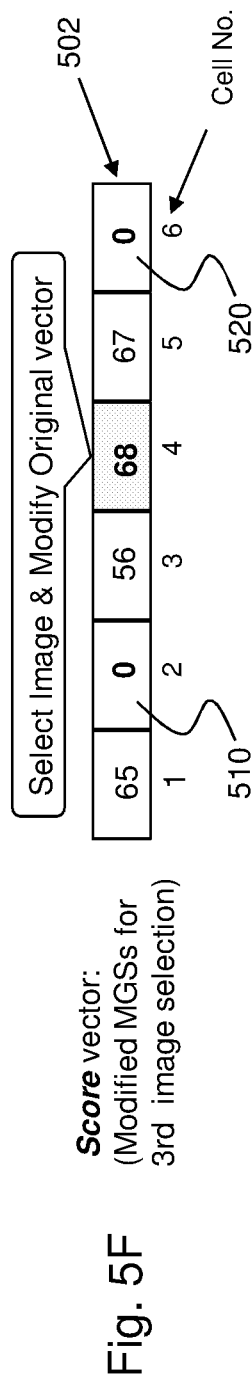

FIGS. 5D-5F demonstrate the effect of an example de-escalating modification (suppression) process on the MGSs content of example score vector 502 of FIG. 5C. FIG. 5D shows the original (unmodified, or unsuppressed) set of MGSs that are used in the selection of the first image. (The first image is selected using the original MGS values.) FIG. 5E shows modified (suppressed) MGSs that are used in the selection of the second image. (The second image is selected after the (original) MGS values are modified, or suppressed, with respect to the first selected image.) FIG. 5F shows modified (suppressed) MGSs that are used in the selection of the third image. (The third image is selected after the (original) MGS values are modified, or suppressed, with respect to the first and second selected images, using the minimum distance, Dmin, identified between the third image and the nearest selected image.)

Referring to FIG. 5D, the (original) score value 90 is currently the greatest MGS (e.g., MGS=90=MGS|max) in score vector 502. Therefore, the image resulting in this score value (the image related to this MGS) is selected. After the image is selected, this score value is zeroed out to ensure that the selected image will not be selected again. FIG. 5E shows, at 510, the greatest score value 90 zeroed out. FIG. 5E also shows the other MGSs in score vector 502 which are modified version of the original MGSs shown in FIG. 5D.

As described herein, the score value modification (suppression) process variably modifies the score values (MGSs) of images in a de-escalating way. By way of example, score value 80 in vector cell No. 1 in FIG. 5D is adjacent to score value 90 in cell No. 2, but score value 78 in vector cell No. 6 in FIG. 5D is the farthest from score value 90 in cell No. 2. Assuming that MGS=80 is related to an image that is much closer to the selected image (e.g., to the image related to MGS=90) than the image related to MGS=78, MGS=80 in vector cell No. 1 (FIG. 5D) is rigorously reduced (the reduced value is shown in FIG. 5E, cell 1) by a relatively large number, for example from 80 to 65. However, the MGS=78 (in vector cell No. 6 (FIG. 5D)), which is related to the remote image, is leniently (moderately, or somewhat) reduced (the reduced value is shown in FIG. 5E, cell 6) by a relatively small number, for example from 78 to 76. The rest of the MGSs may be modified (reduced) using the same principle.

After the first MGSs modification process is performed, the next (in this case the second) image may be selected based on the modified score values. Referring to FIG. 5E, among the modified score values (among the modified MGSs) the score value '76' is the greatest (MGS=76=MGS|max), so the image resulting in this score value may be selected, and, after the second image is selected, the score value related to it (score value 76) may be zeroed out, or otherwise manipulated, to ensure that the second image will not be selected again. FIG. 5F shows, at 520, the greatest score value 76 zeroed out. FIG. 5F also shows the other MGSs in score vector 502 which are modified version of the original MGSs shown in FIG. 5D.

Every original MGS in FIG. 5D may be modified differently from one image selection to another, because an original MGS of an unselected image is modified based on Dmin, which is a distance between its related image and the nearest selected image, and the distances between unselected images and already selected images may change as more and more images are selected. After the second MGSs modification process is performed, the next (at this stage the third) image may be selected based on the (new) modified score values. Referring to FIG. 5F, among the modified score values the score value 68 (cell No. 4. FIG. 5F) is the greatest (MGS=68=MGS|max), so the image resulting in this score value may be selected. If the image selection budget includes only three images, the images selection process may be terminated at this stage. However, if the image budget is larger and the score vector includes more (say, hundreds or thousands of) MGSs that are respectively related to as many images, the images selection process may continue in a similar way until the image budget is used up.

The image selection methods disclosed herein (for example in FIGS. 6A-6B, and in FIG. 7) in some embodiments guarantee that: (1) the total number of selected images does not exceed a predetermined number of images (e.g., an image budget), (2) the selected images include the most clinically important pathologies, and (3) the image selection processes disclosed herein can be 'fine-tuned' to select (e.g., for analysis or for displaying): (3.1) only images that were captured from a particular segment or portion of the GI system, and/or (3.2) images that include a particular type of pathology (e.g., polyps).

Figure 8:
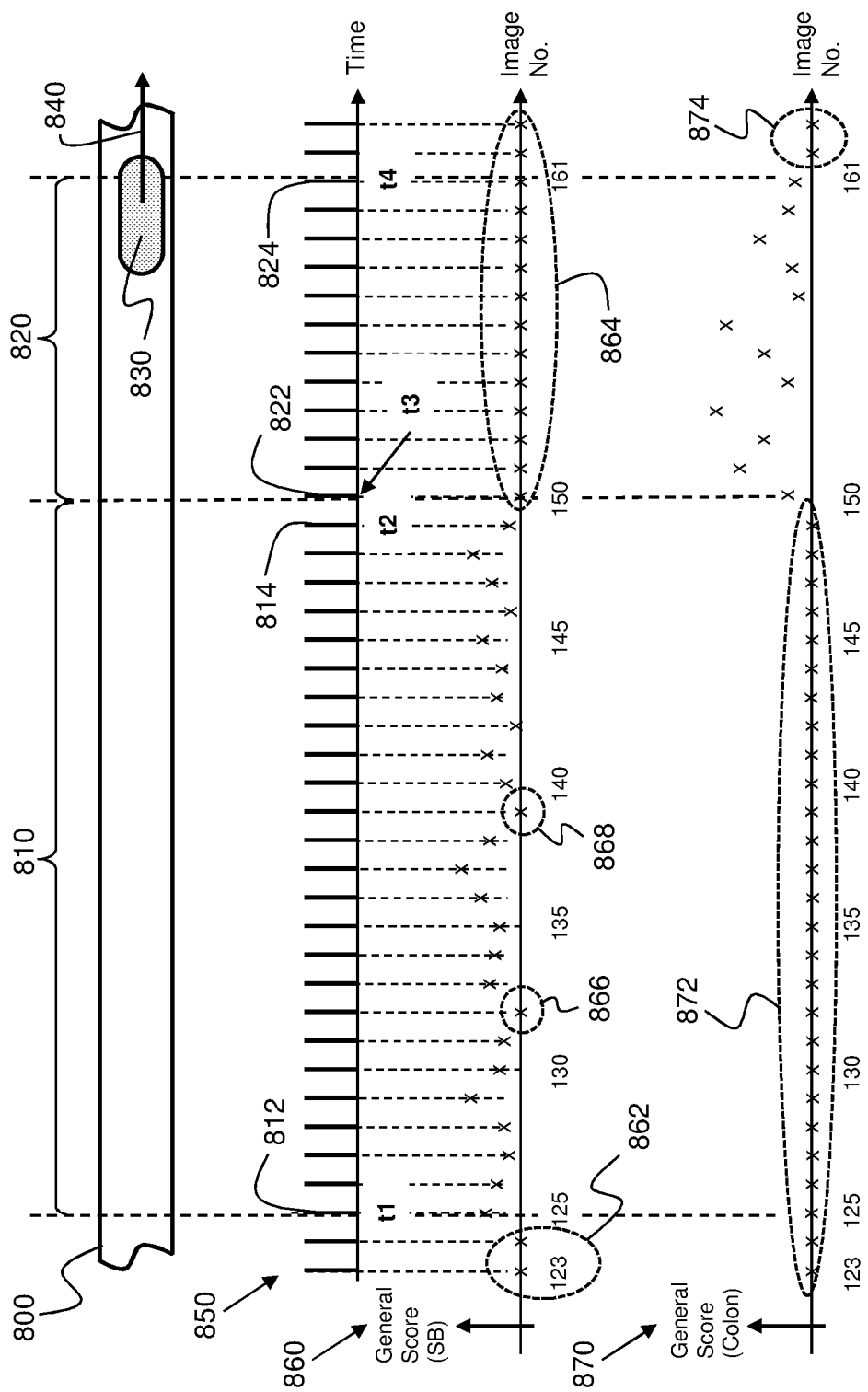
FIG. 8 schematically illustrates an example implementation of the image selection method according to an example embodiment.

The particular segment or portion of the GI system may be relatively long (e.g., small bowel), or relatively short (e.g., colon). The image selection process may be fine-tuned to select only images that were taken from a particular segment of the small bowel, or from a particular segment of the colon, or from any other GI segment of interest. Finetuning the image selection process to selectively select images that were taken from a particular GI section may be performed by, for example, zeroing out the extraneous score values of all the images that were taken outside the GI segment of interest. (An example of such selective image selection process is shown in FIG. 8, which is described below.)

Figure 6C:
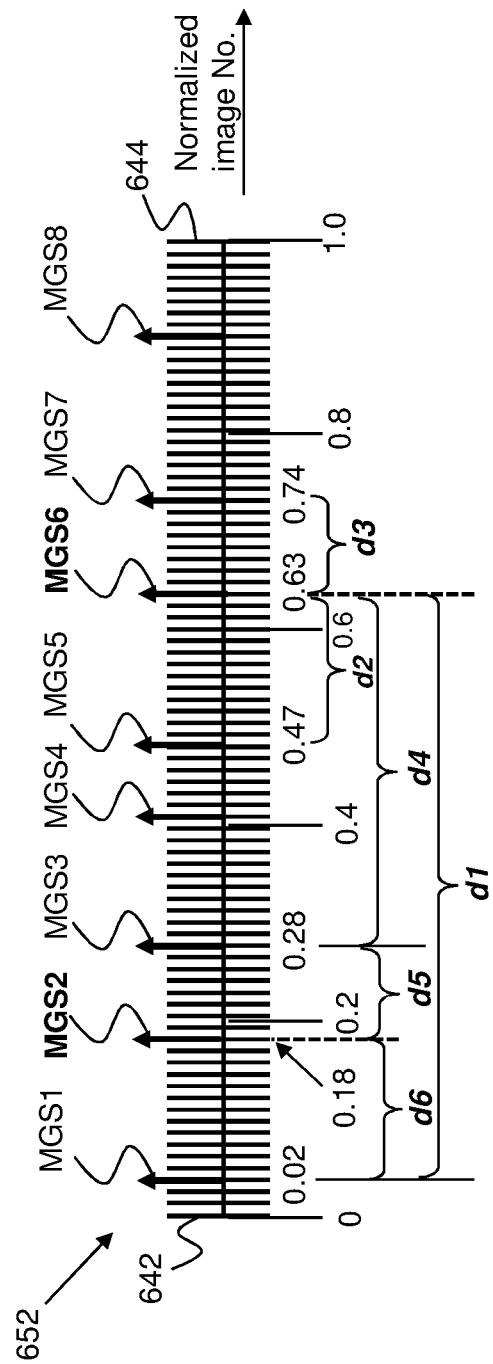
FIG. 6C demonstrates calculation of distances between images according to an example embodiment.
Figure 6A:
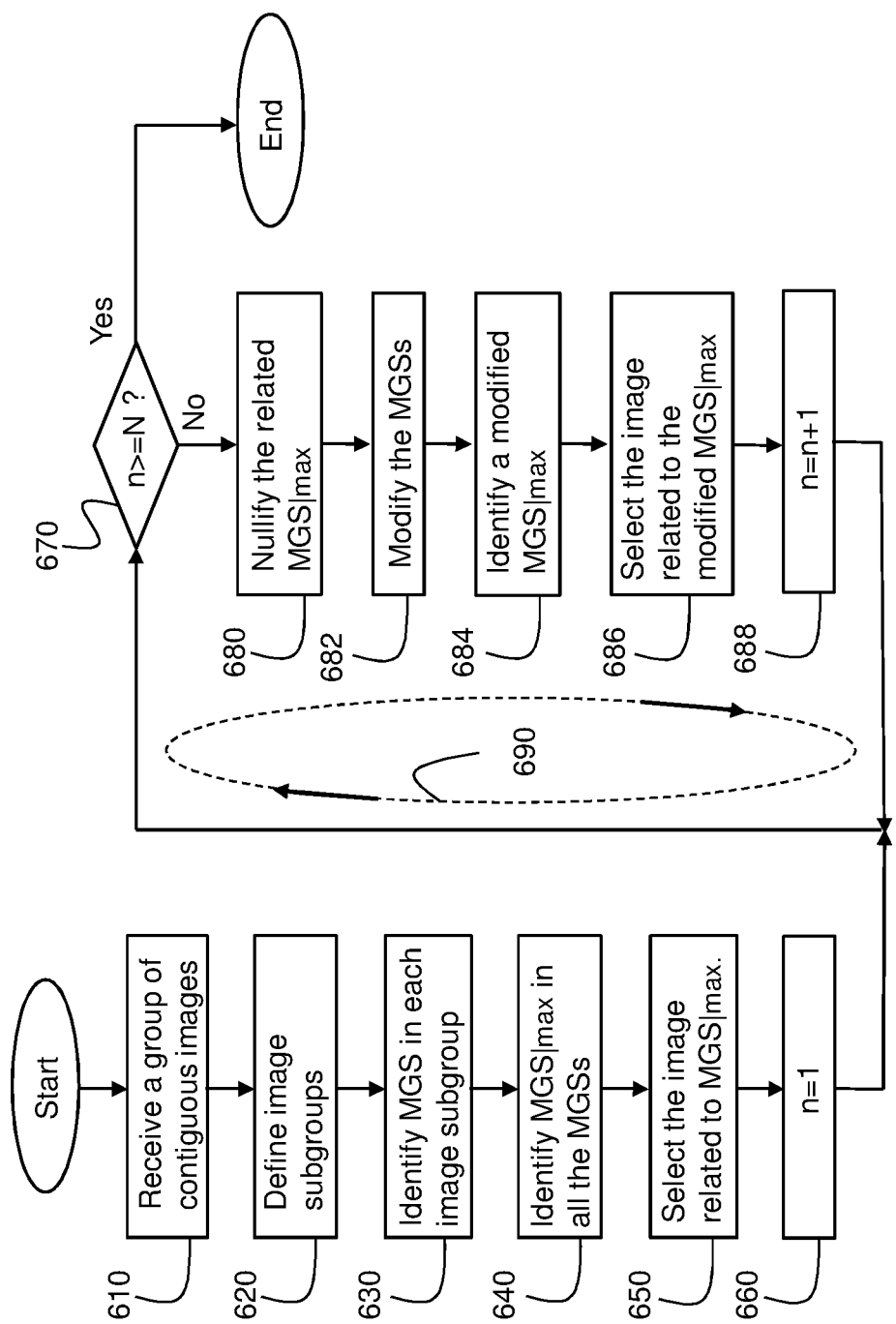
FIG. 6A shows a method for selecting images originating from one imager according to an example embodiment.

FIG. 6A shows a method of selecting images for display (or for any other purpose) according to an example embodiment of the invention. FIG. 6A is described in association with FIG. 1 and FIG. 3. The image selection method of FIG. 6A is applicable to a group of images that is obtained in vivo from one imager (e.g., Imager-1, FIG. 2) of an in-vivo device. The embodiment shown in FIG. 6A includes an image selection iteration or repetition loop (690) that selects images (for example for further processing, analysis and/or for display), one image per iteration/repetition.

At step 610, data processor 14 may receive a group of contiguous images (e.g., group 300) contiguously captured in-vivo by in-vivo device 40 in a body lumen. Data processor 14 may calculate, at step 610 or in a separate step, for each image in the image group, a general score (GS) that may indicate a probability that the image includes at least one type of pathology. Data processor 14 may receive a GS value for each image with the image, or it may calculate it 'in-situ' as a function of scores that the pathology detectors D1, . . . , Dm (pathology detectors 15, FIG. 1) may output for the images. Alternatively, data processor 14 may not need the images but, instead, obtain only the GSs related to the images and, in addition, data processor 14 may obtain information regarding the relative location of each image in the image group.

At step 620, data processor 14 may partition the image group into image subgroups such that each image subgroup includes a base image (e.g., base images 330, 340 and 350 in FIG. 3) and subsequent images that resemble or are similar to the base image. (Partitioning an image group may be performed, for example, in the way described in connection with FIG. 3.)

As each image subgroup may include many images, where with each image is associated a general score, data processor 14 identifies, at step 630, in each image subgroup the general score having the highest value. (The general score having the highest value in an image subgroup is referred to herein as the maximum general score (MGS) of the image subgroup.)

At step 640, data processor 14 identifies MGS|max, which is the MGS having the highest value among all the MGSs of the image subgroups, and, at step 650, data processor 14 may select the image that is related to MGS|max, for example for further processing (e.g., analysis) and/or for display, and assign the value one to a loop counter n (at step 660).

At step 670 data processor 14 checks whether the number of already selected images is N, which is the number of images permitted for selection by a predetermined image budget. If the image budget has already been used up, that is, if n≥N (this condition is shown as "Yes" at step 670), processor 14 may terminate the image selection process and, for example, analyze only the selected images, or display the selected images, for example, in a separate display window. However, if the image budget has not been used up, that is, if n<N (this condition is shown as "No" at step 670), processor 14 may nullify, at step 680, the value of the MGS|max of (e.g. associated with, or calculated for) the selected image, to ensure that the currently selected image will not be selected again, thus giving a chance to other images to be selected. ('Nullify', in the context of the invention, means setting a value of a MGS|max to a value; e.g., to zero or to a negative value, that reduces to zero the probability that the related image would be selected again.) It is noted that a score threshold may be used instead of, or in combination with, the predetermined number N of images, as described, for example, in connection with step 616 of FIG. 6B, which is described below.

At step 682, processor 14 may modify the (original) MGSs of the image subgroups such that the value of each particular (original) MGS changes (for example, by reducing its value by processor 14) based on a distance that exists between the image that is related to the particular original MGS and a nearest already selected image. For example, the closer a candidate image is to the nearest selected image, the more the value of the MGS related to the candidate image is reduced. (A 'candidate image', as used herein, is any image in an image subgroup, whose general score has been identified, for example by data processor 14, to be an MGS, and the image has not been selected yet, though it may be selected in some other repetition 690, or not selected at all, hence the adjective 'candidate' in 'candidate image'.) For example, as at this stage only one image has been selected (n=1), each MGS is modified depending on the distance between its related (candidate) image and the one selected image, and the modification 'factor', or process, de-escalates with distance from the selected image. (Throughout the specification, modification of an MGS means modification of an original MGS, and a 'modified' MGS is an MGS having a value which is reduced, or lowered, relative to a corresponding original MGS. An original MGS and a modified version of the original MGS are both related to a same image.)

At step 684 (after the MGSs are modified), data processor 14 may identify a modified MGS that currently has the greatest value (that is. MGS|max) among the modified MGSs. At step 686, data processor 14 may select the image related to the new identified MGS|max. At step 688, data processor 14 may increment the loop counter, n, by one, in each repetition, until all the image budget is used (that is, until n=N, e.g., N=100).

If at step 670 the value of the loop counter, n, is still less than N, data processor 14 may nullify, at step 680, the MGS|max that is related to the last image that was selected, then modify, at step 682, each MGS based on the distance between the image related to the MGS and the nearest selected image. For example, if two images 'A' and 'B' (e.g., out of an image budget of, for example, ten images) have already been selected, then every particular MGS is modified according to a distance, d, between the image related to the particular MGS and the nearest selected image. For example, if the image related to the particular MGS is closer to, say, image 'A', then the distance, d, between the image related to the particular MGS and image 'A' is used to modify the particular MGS, and, as described herein, the shorter d, the greater the reduction in the value of the particular MGS. Every time data processor 14 performs loop 690 to select an image, the (original) MGSs are modified in a different way because the distances between candidate images and selected images, which are the basis for the MGSs modification process, change every time another image is selected.

A variant of the embodiment shown in FIG. 6A may include steps ordered as shown in FIG. 6A, and the images selection process may include: (i) identifying, according to step 640 (or step 684, depending on the stage of the process), the greatest MGS (MGS|max) in the MGSs identified for the image subgroups and, according to step 650 (or step 686, depending on the stage of the process), selecting the image related to the greatest MGS; (ii) nullifying, according to step 680, the MGS identified at step 640 (or at step 684) related to the selected image; (iii) modifying, according to step 682, each MGS (original MGSs based on a distance d between an image related to the particular MGS and each selected image; (iv) identifying, according to step 684, in the modified MGSs, a modified MGS which has the maximum value (e.g., MGS|max). An embodiment of the method may further include selecting, according to step 686, the image that is related to that modified MGS|max, and repeating steps (ii)-(iv) until a predetermined criterion selected from a group consisting of a number N of images and a score threshold is met.

Figure 6B:
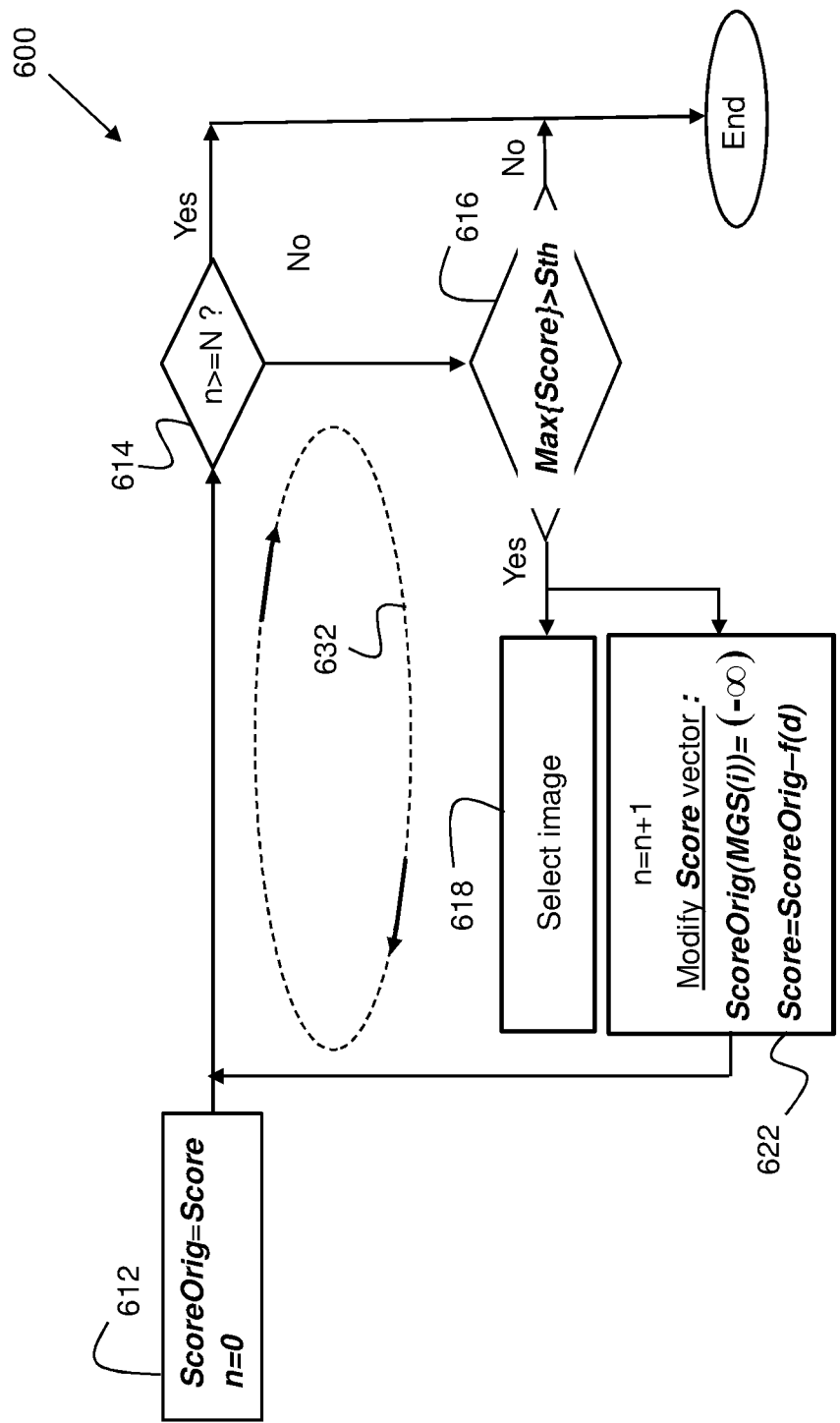
FIG. 6B shows a method for selecting images originating from one imager according to another example embodiment.

FIG. 6B shows an example implementation of the image selection method of FIG. 6A. FIG. 6B is described in association with FIG. 1 and FIG. 6A. 'Score' is a score vector initially including original MGSs for multiple image subgroups (e.g., one MGS per image subgroup). Vector 'Score' may also include modified MGSs during the image selection process.

'ScoreOrig' is a score vector holding the original MGSs for each image selection repetition loop (e.g., repetition loops 690 and 632). The entire content of the Score vector may change as a result of the modification of the MGSs every time an image is selected. The content of the Score-Orig vector, on the other hand, changes one MGS at a time due to the nullification of one MGS every time an image related to this particular MGS is selected. (In every repetition, another MGS, which is currently identified as MGS|max, is nullified, until N MGSs in the vector ScoreOrig are nullified.)

At step 612, data processor 14 initializes vector ScoreOrig with the original MGSs that are initially stored/contained in vector Score. At step 612 data processor 14 may also reset a loop counter, n, to, or initializes it with, a reference number, for example zero.

At step 614, data processor 14 checks if a number N of images have been selected (it checks whether the image budget has been used up). If N images have already been selected (the condition is shown as "Yes" at step 614), data processor 14 may terminate the image selection process. However, if less than N images have been selected (the condition is shown as "No" at step 614), data processor 14 may, at step 616, identify, in the Score vector, the MGS currently having the maximum value (that is, MGS|max). If a MGS|max has been found but its value is lower than a predetermined score threshold, St, (e.g., if MGS|max is equal to zero, or if it is negative), the condition is shown as "No" at step 616, data processor 14 may terminate the images selection process. However, if the identified MGS|max is greater than the score threshold St (the condition is shown as "Yes" at step 616), data processor 14 may select, at step 618, the image related to the MGS currently identified as the MGS|max. In some embodiments, iteration/repetition loop 632 may not include step 614 (e.g., this step may be skipped, removed or ignored), and the number of images ultimately selected may depend on the value of Sth. (The lower the Sth, the greater the number of selected images.) Therefore, by using only the score threshold, Sth, or using both the image count limit N (at steps 614) and the score threshold Sth (at step 616), the number of images ultimately selected by the process may be known only post factum; that is, only after the image selection process is completed. However, the user may change, or set, the value of the score threshold to reduce or increase the number of images to be selected, and the user may also limit the number of images to a desired number by setting a corresponding value to the parameter N.

At step 622, data processor 14 may nullify, in the vector ScoreOrig, the MGS that it currently identifies as the MGS|max, for example by replacing the value MGS|max in vector ScoreOrig with, for example, the value (−∞), or with the value zero, in order to exclude this image from the image selection process (to ensure that this image will not be selected more than once). Then (still at step 622, or in a separate step), data processor 14 retrieves MGSs from the vector ScoreOrig, and modifies the retrieved MGSs by using a modification function $f(d)$. Finally, data processor 14 stores the modified MGSs in the Score vector, thus updating the content of the Score vector with new modified MGSs values every time a new image is selected at step 618.

If the allocated image budget has not been used up (per step 614), the next greatest MGS (MGS|max) among the modified MGSs is identified, at step 616, and the image related to MGS|max (among the modified MGSs) is selected, at step 618, and so on.

Modifying Original MGSs and GSs

The modification function $f(d)$ factors in distances (e.g., in terms of number of images that intervene, or are temporally interposed) between an image just selected for display and candidate images in the image group. In some embodiments, modification function $f(d)$ may be devised such that the closer a candidate image is to a currently selected image, the greater is the function's output value, and, therefore, the lower the value of the MGS subject of the modification process. For example, assume that images are numbered in the order of their capture, and an example image number 250 has just been selected for display. Continuing the example, an example image number 290 in the group of images is 40 images away from image number 250 (d=290−250=40 images), and an example image number 100 in the series of images is 150 images away from image number 250 (d=|100−250|=150 images). The function $f(d)$ may be selected (configured) such that the score value of the closer image (in this example the score value of image number 290) would be rigorously suppressed (substantially lowered) by the function $f(d)$ outputting, for image 290, a relatively high number (for example 45). In contrast, the score value of example image 100 would be only leniently (less rigorously, or somewhat) 'suppressed' by function $f(d)$, for example by the function $f(d)$ outputting, for image 100, a relatively low number (for example 12). (As shown in FIG. 6B, a modified score may be calculated, for example, by using the formula Score-ScorOrig-ftd), cf. step 622. Therefore, the greater the value of $f(d)$, the smaller the value of Score, and, therefore, the greater the modification of the original score.)

The rationale behind the distance-dependent MGSs modification process is that if a candidate image near an already selected frame is clinically very important (which is indicated or inferred by its relatively high MGS value), there would still be a good chance for the near image, even after its MGS value is made smaller rigorously, to be selected in a next iteration or repetition. However, if the candidate image near the selected image is of low clinical importance, which may be reflected in its relatively low score value, or if it is as clinically important as the selected image, it may be beneficial to 'skip' it (skip the near candidate image by reducing its chance to be selected) by lowering its score value so that a candidate image that is relatively far from the selected image may have a better chance to be selected even if the far candidate image and the near candidate image may be similar in terms of clinical importance. Put differently, it may be beneficial to select for display an image that is near a selected image only if the original MGS value of the near image is relatively very high, which indicates or infers that the near image is clinically very important, so that lowering, even significantly, the high score value of the near image would, in such a case, still give that image a chance to be selected in the next image selection iteration/repetition. Another rational is that the closer an image is to an already selected image, the greater is the probability that the selected image and the image near the selected image show or include a same pathology, so it may be beneficial to ultimately select only one image of the two in favor of images that may show other pathologies somewhere else in the body lumen.

It may be that a selected image is selected because its related polyp score has a high value, and an image near the selected image has high score value because of bleeding. In such a case, in order to ensure that both images (which are related to different pathologies) are selected, the score's suppression process may be applied to scores selectively; that is, it may be applied only to scores that are related to a same type of pathology (e.g., to polyps, or to bleeding, etc.).

The modification function, $f(d)$, may be any function that reduces the value of an MGS as a function of the distance, d, between an image related to the MGS and a nearest image that was already (previously) selected. The modification function, $f(d)$, may be devised such that the shorter the distance, d, between the two instances (the image related to a MGS and the selected image which is the nearest to that image), the greater (the more rigorous) the reduction in the value of the MGS. The function, $f(d)$, may be linear (e.g., $f(d)=a*d$, where 'a' is a coefficient), or non-linear (e.g., $f(d)=a*d^2+b*d+c$, where 'a' and 'b' are coefficients and 'c' is a constant). The function, $f(d)$, may be Gaussian exponent, or exponent with an absolute value of distance, or a step function, or triangularly shaped with its apex, or peak, located at a selected frame/image and linearly decreases with distance.

The distance, d, between images (for example between an image related to an MGS and a selected image) may be calculated or measured in units of: (i) time, or (ii) a number of intervening images, or (iii) a number of intervening image subgroups, or (iv) a distance that the in-vivo device traveled in the body lumen while taking the images, or (v) a distance that the in-vivo device traveled in the body lumen with respect to a marked landmark in the group of images, corresponding to a landmark in the body lumen, or (vi) percentage of a video clip including all, or most of, the group of contiguous images, or (vii) estimated distance (e.g., via linear progress or similar techniques).

Each of the unit instances described above may be calculated or measured as: (i) an absolute value, for example as a value that may be calculated or measured relative to a beginning of the group of contiguous images, or relative to a beginning of the body lumen, or relative to any landmark in the group of contiguous images or in the body lumen, or (ii) a percentage, for example as a percentage of the entire group of contiguous images, or as a percentage of the body lumen or portion of the body lumen, or (iii) a percentage of a video clip including all, or most of, the group of contiguous images, or (iv) a percentage of a distance traveled by the in-vivo device, or (v) a percentage of a time traveled by the in-vivo device, for example a percentage of time it takes the in-vivo device to traverse a distance captured in a certain series of images). The body lumen may be the GI tract or an organ of the GI system.

Data processor 14 may enable a user (e.g., a physician) to select a modification function according to the part of the body lumen from which images were taken, and this may be beneficial because, by selecting a suitable modification function, the user may bias the image selection process towards (to 'favor', or to give preference to) a particular part of the body lumen the user is more interested in by, for example, leniently (somewhat) reducing the values of the MGSs related to (originating from) the focused on lumen part, while rigorously reducing the values of the MGSs originating from other lumen parts.

FIG. 6C demonstrates an example group 652 of contiguous images according to an example embodiment. FIG. 6C is described in association with FIG. 6B. Assume that image group 652 includes a large number of (for example 100,000) contiguous images. The large number of images may be normalized such that each image has a normalized image number. For example, the image captured first (the image shown at 642) may be assigned the value 0.00, and the image captured last (the image is shown at 644) may be assigned the value 1.00. Also assume that a score vector similar to the vector Score of FIG. 6B includes eight MGSs, designates, in FIG. 6C, as $MGS_1$, $MGS_2$, ..., $MGS_8$, that respectively correspond to eight images, and that the number of images to select (for example for further analysis and/or for display) is three, that is, assume that N=3).

Assume that, per step 616 of FIG. 6B, the value of $MGS_6$ is currently the highest among $MGS_1$, $MGS_2$, ..., $MGS_8$ (e.g., $MGS_6$=MGS|max), and, therefore, assume that, per step 618, the image related to $MGS_6$ is the first image that is selected. At step 622, the value of $MGS_6$ is nullified (in the related score vector ScoreOrg.), and each $MGS_i$ of $MGS_1$, $MGS_2$, ..., $MGS_8$ is modified based on the distance, d, between the image related to the $MGS_i$ and a nearest selected image. (At this stage only one image (image 0.63 corresponding to $MGS_6$) was selected, so all MGSs are modified with respect with this image.) For example, the distance d1 between the image related to $MGS_1$ and the selected image related to $MGS_6$ is 0.61 (d1=0.63−0.02=0.61). Similarly, the distance d2 between the image related to MGSs and the selected image related to $MGS_6$ is 1.016 (d2=0.63−0.47=0.16). Similarly, the distance d3 between the image related to $MGS_7$ and the selected image related to $MGS_6$ is 0.11 (d3=0.74−0.63=0.11), the distance d4 between the image related to $MGS_3$ and the selected image related to $MGS_6$ is 0.45 (d4=0.63−0.18=0.45), and so on. (The distances of the other MGSs may be found in the same way.) Each MGS is, then, modified according to the distance of its related image from the selected image. If the images budget has not yet been used up (per step 614, FIG. 6B), then after all MGSs are modified, per step 622, to result in modified values $MGS'_1$, $MGS'_2$, $MGS'_3$, $MGS'_4$, $MGS'_5$, $MGS'_6$ ($MGS_6$ is nullified), $MGS'_7$, $MGS'_8$, a maximum MGS (that is, MGS|max) is identified, at step 616, among the modified MGSs, and the image (at this stage the second image) related to the identified MGS|max among the modified MGSs is selected at step 618. Assume that the modified MGS currently having the greatest value is $MGS'_2$ (that is, $MGS'_2$=MGS|max) and, therefore, the second selected image is the image related to $MGS'_2$.

After the second image (the image related to $MGS'_2$ and $MGS_2$) is selected (at step 618), the original $MGS_2$ is nullified (in the score vector ScoreOrg, at step 622), and the distance between each image that is related to each of the other (the non-nullified) MGSs and each selected images is calculated in order to identify, for each candidate image, the nearest selected image. Then, each original MGS is modified again, this time according to a distance between the particular image related to each modified MGS and the selected image that is the nearest to the particular image. In other words, as more images are selected using the image selection process, the distances, based on which the MGSs are modified, may change. For example, after image (normalized) number 0.63 is selected as the first image (because its $MGS_6$ is the greatest), image number 0.28 is at distance d4 from image number 0.63, so $MGS_3$ (the MGS of image number 0.28) is modified according to distance d4. However, after image number 0.18, corresponding to $MGS_2$, is selected as the second image (because $MGS'_2$ is the new greatest MGS in the second selection repetition), the distance d5 between image number 0.28 and image number 0.18 is shorter than the distance d4 between image number 0.28 and image number 0.63. (Distance d5=0.10, distance d4=0.35.) Therefore, the value of original $MGS_3$ is modified, after the second image is selected, according to the distance d5, which is the distance from image number 0.28 to the nearest selected image. Similarly, after the second image (image number 0.18) is selected, image number 0.02 is closer to selected image 0.18 than to selected image 0.63 (d6<d1). Therefore, the original MGS|related to image number 0.02 is modified, after the selection of the second image, using distance d6. (After selection of the first image the original $MGS_1$ is modified using distance d1.)

In one embodiment the same distance calculation process applies to all other MGSs and every time a new image is selected. (As described herein, distances between candidate images may be calculated or measured in units of time (e.g., capture time of images being compared), number of intervening images, number of image subgroups, and, in fact, any suitable technique.)

Referring to FIGS. 6A-6B, formula (4) is an example scores (MGSs) modification function, and formula (5) is an example formula showing an example way of using $f(d)$ to modify the (original) MGSs:

$$f(d=D\min(i))=(-30)*\exp.\{-(1.000*D\min(i))^2\} \quad (4)$$

$$Score(i)=ScoreOrig(i)-30*\exp.\{-(1,000*D\min(i))^2\} \quad (5)$$

where ScoreOrig(i) (i=1, 2, 3, . . . ) is an original MGS(i) value in score vector ScoreOrig, Dmin(i) is a distance, d, between an image related to MGS(i) and the nearest selected image, and Score(i) is a new score resulting from the modification of the corresponding (original) MGS. (Dmin(i) may have a value, for example, in the range of [0.0.1.0], which is in accordance with FIG. 6C.) As described herein, after two or more images are selected, a candidate image may be closest to one particular selected image, and Dmin(i) designates the distance between the candidate image and the closest selected image. Referring to formula (5), the shorter is d (the smaller the value of Dmin(i)), the greater the value that is detracted or removed from ScoreOrig(i). (The more rigorously the related MGS is modified.)

While some method(s) described herein, for example in connection with FIGS. 6A-6B, are applicable to an in-vivo device including one imager, embodiments may be generalized to an in-vivo device that includes any number, q, of imagers, as described below. Briefly, while an in-vivo device with one imager produces one image group that produces one MGS|max value at a time (e.g., in each image selection repetition 690, FIG. 6A), an in-vivo device with many imagers produces as many image groups that produce as many MGS|max values at a time, and, each time (e.g., during each image selection repetition 770, FIG. 7), the greatest MGS|max among all the MGS|max values is identified, and the image related to the greatest MGS|max is selected. By way of example, a method for selecting images from a number q of groups of contiguous images may include performing, for q groups of contiguous images respectively captured in a body lumen by q imagers, where each image of each group may be associated to a general score (GS) indicative of a probability that the image includes at least one type of pathology, and to a distance, d, indicative of a distance between images of the respective group, may include, for each image group of the q groups of contiguous images: (A) dividing, or separating, the image group, or a portion thereof, into image subgroups, each image subgroup including a base image and images resembling to the base image, and (B) identifying a set Set(i) (i=1, 2, 3, . . . ) of maximum general scores (MGSs), the set Set(i) of maximum general scores including a maximum general score (MGS) for each image subgroup of the image group, and selecting images for processing, wherein the image selection may include: (i) identifying a maximum MGS (MGS|max) in each set S(i) of MGSs; (ii) identifying, among all the MGSs|max, the greatest MGS|max, and selecting the image related to the greatest MGS|max; (iii) nullifying the greatest MGS|max related to the selected image; (iv) modifying the particular set Set(i) of MGSs related to the selected image based on a distance d between images respectively related to the MGSs of the particular set Set(i) of MGSs and each selected image; and repeating steps (i)-(iv) until a predetermined criterion selected from a group consisting of a maximum number, N. of images and a score threshold. Sth, is met. An example method for a case where the number q of imagers, and thus of groups of contiguous images, is equal to two, is described in connection with FIG. 7, which is described below.

Figure 7:
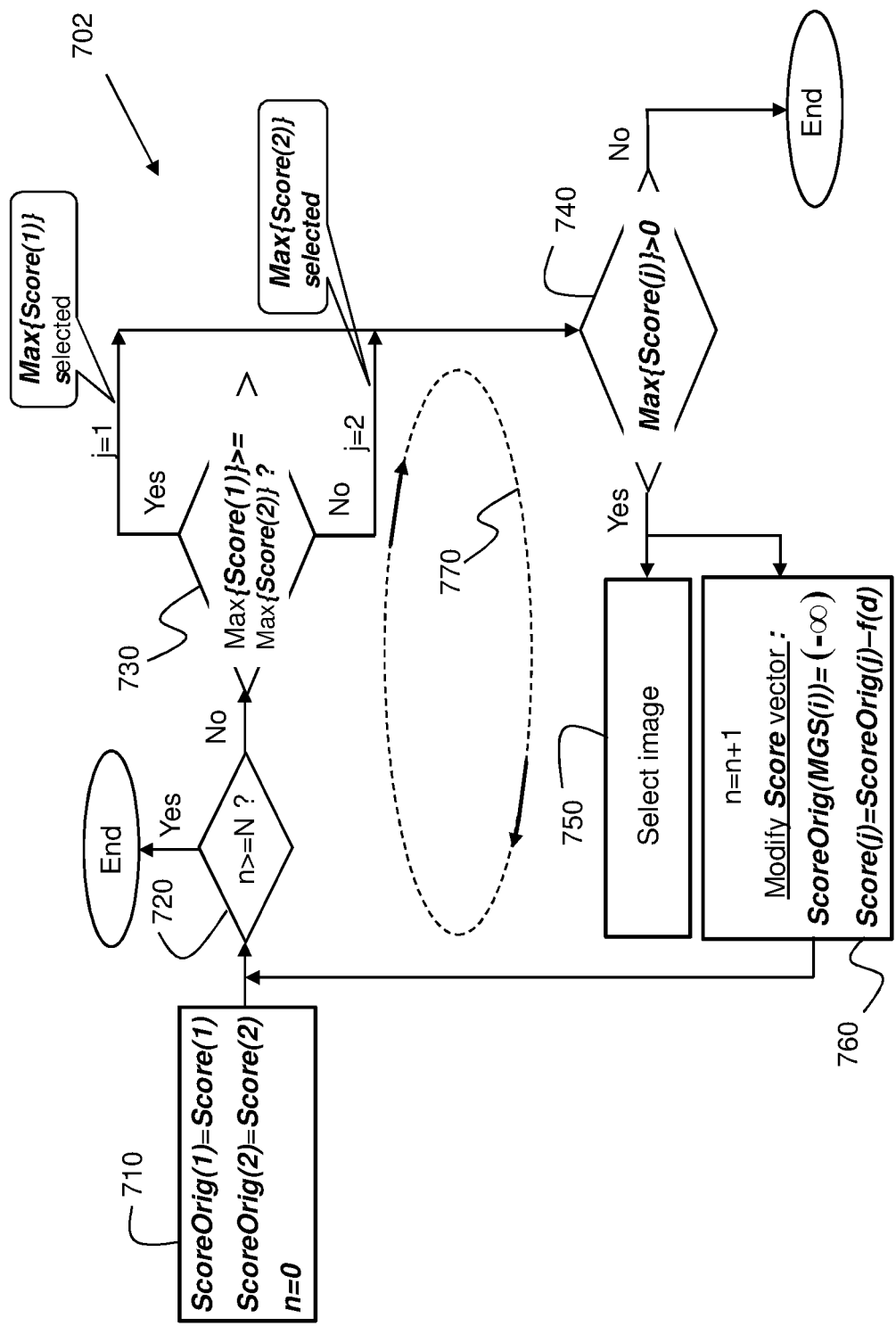
FIG. 7 shows a method for selecting images originating from two imagers according to another example embodiment.

FIG. 7 shows a method for selecting images for display according to another embodiment of the invention. FIG. 7 is described in association with FIG. 1. The images' selection method of FIG. 7 is applied to two image groups respectively obtained in vivo from two imagers (e.g., Imager-1 and Imager-2, FIG. 2) of an in-vivo device. (FIG. 7 refers to a system configuration where the in-vivo device includes two imagers.) The embodiment shown in FIG. 7 may include an iteration or repetition loop (770) to select images for display (or for other purposes; e.g., for further analysis), one image per iteration/repetition. Each iteration/repetition may result in the selection of an image that originates from one of the two imagers. One imager may ultimately provide more (selected) images than the other imager, and the images' selection method in some embodiments guarantees that the total number of images selected from both imagers does not exceed the allocated images budget. As described in connection with step 616 of FIG. 6B, using an 'image budget' or limit may include completing the image selection process when the number of selected images is equal to a predetermined number, N. of images, or it may include using a score threshold. Sth. or it may include using both predetermined number, N, of images, and a score threshold in combination. Using a score threshold (Sth), in some embodiments, guarantees selection of some finite (though unknown in advance) number of images because the values of the MGSs decrease from one image selection loop to another, so that, at some point, a remaining maximum MGS would necessarily be, after a finite number of iterations 770, smaller than the score threshold.

After images originating from the two imagers are pathology-wise processed (e.g., by data processor 14, or by a remote computer) in the way described herein, each image group is independently partitioned into image subgroups. Data processor 14 may identify one or more local maxima scores, MGSs, in each image subgroup of each image group, and data processor 14 may create two score vectors for separately accommodating the two sets of MGSs: (1) a score vector Score(1) for accommodating the original MGSs originating from the image group (image subgroups) associated with the first imager, and (2) a score vector Score(2) for accommodating the original MGSs originating from the image group (image subgroups) associated with the second imager. Each score vector Score(j) (where j=1, 2) may include a plurality of local maxima score values. MGSs. In some embodiments, every local maxima score value, MGS, in every image subgroup (in both image groups) is stored in the respective vector Score(j). (The index 'i', as used herein, indicates single vector value; e.g., Score(i) is an individual score value. The index 'j' indicates a whole vector, e.g., Score(j) is a vector including multiple score values.) In other embodiments, only the greatest local maxima score value. MGS, in each image subgroup is stored in the respective vector Score(j). In other embodiments, the greatest score value in each image subgroup is selected for the respective vector Score(j) regardless of whether it is, or it is not, a local maxima score value.

At step 710, data processor 14 may initialize a score vector ScoreOrig(1) associated with a first imager with the (original) MGSs values that are initially stored in score vector Score(1), and, similarly, it may also initialize a score vector ScoreOrig(2) associated with a second imager with the (original) MGSs values that are initially stored in vector Score(2). The MGSs initially stored in each of score vector ScoreOrig(1) and score vector ScoreOrig(2) are referred to herein as 'original MGSs'. Modified MGSs are stored in score vector Score(1) and in score vector Score(2). (The (original) MGSs values stored in score vector Score(1) change every time an image is selected from images which are related to MGSs that are stored in this vector. Similarly, the (original) MGSs values stored in score vector Score(2) change every time an image is selected from images which are related to MGSs that are stored in this vector.) At step 710 data processor 14 may also reset a loop counter, n, to an initial value; e.g., to one.

At step 720 data processor 14 may check if a number of N images have been selected (the processor may check whether the image budget has been used up). If N images have already been selected (the condition is shown as "Yes" at step 720), data processor 14 may terminate the image selection process. However, if less than N images have been selected (the condition is shown as "No" at step 720), data processor 14 may, at step 730, identify in each score vector Score(j) the MGS currently having the maximum value (this MGS is referred to herein as 'MGSlmax'). Namely, data processor 14 may identify MGSlmax(1) in score Score(1), and MGSlmax(2) in score Score(2). Then, data processor 14 may select from MGSlmax(1) and MGSlmax(2) the MGSlmax(i) having the highest value. If MGSlmax(1) is equal to or greater than MGSlmax(2) (this condition is shown as "Yes" at step 730; j=1), the MGSs modification process performed at step 760 will be applied to the original MGSs associated with the first imager (to the original MGSs stored in score vector ScoreOrig(1)), and if MGSlmax(2) is greater than MGSlmax(1) (this condition is shown as "No" at step 730; j=2), the MGSs modification process will be applied to the original MGSs associated with the second imager (the original MGSs stored in score vector ScoreOrig(2)).

At step 740, if the value of the selected MGSlmax(i), where i=1 or i=2 (depending on which MGSlmax(i) is greater: MGSlmax(1) or MGSlmax(2)), is equal to zero, or it is negative, or, in a general case if it is lower than a predetermined positive score value threshold, (the condition is shown as "No" at step 740), data processor 14 may terminate the images selection process. (Depending on the value of the score threshold, it may occur that the image selection process is terminated before N images are selected.) However, if the selected MGSlmax(i) is greater than zero (the condition is shown as "Yes" at step 740), or if it is greater than the score threshold, data processor 14 may select, at step 750, the image related to the MGSlmax(i) currently identified as the greatest MGSlmax among the current MGSlmax(1) and MGSlmax(2). (The values of MGSlmax(1) and MGSlmax(2) may change from one repetition loop 770 to another.)

At step 760, data processor 14 may nullify, in the score vector ScoreOrig(j), the MGS that it currently identified as the greatest MGSlmax(i) in the two score vectors Score(1) and Score(2), in order to exclude the selected image from the image selection process (to ensure that this image will not be selected more than once). Data processor 14 may nullify the MGS by, for example, replacing the value MGSlmax(i) in the associated score vector ScoreOrig(j) with the value (−∞), or with the value zero. Then (still at step 760, or in a separate step), data processor 14 may retrieve the original MGSs from the related score vector ScoreOrig(j) (the score vector ScoreOrig(j) associated with the MGSlmax(i) that was selected at step 730), then modify the retrieved MGSs by using a modification function td), and store the modified MGSs in the respective score vector Score(j), thus updating the scores content of score vector Score(j) with new modified MGSs values every time a new image is selected at step 750 from the corresponding imager.

When step 730 is performed for the first time, both score vectors Score(1) and Score(2) contain (store) original MGSs. Therefore, first execution of step 730 involves identifying, and comparing between, an original MGSlmax(i) in the score vector Score(1) and an original MGSlmax(i) in the score vector Score(2). When the first image is selected at step 750, the related score vector Score(j) in which the related MGSlmax was identified is modified, which process results in modified MGSs in score vector Score(j). Therefore, the second execution of step 730 involves comparing between an original MGSlmax stored in the other, yet unmodified, score vector Score(j) and a modified MGSlmax from the modified score vector Score(j). However, assuming that at a certain point in the image selection process at least one image has been selected from each image group, further executions of step 730 includes comparing between modified MGSlmax values, though in each repetition loop (770) a different score vector Score(j) is modified, and each modification of score vector Score(j) is done with respect to the respective original MGSs.

The image selection methods described herein may be similarly applied to any number q of imagers respectively capturing q groups of images, including to one imager. For a general case where there are q image groups, each group of images may result in one or more image subgroup and related original MGSs. and, in addition, a number q of MGSlmax values (an MGSlmax value per image group) may be compared (at a step similar to step 730) in each image selection iteration or repetition loop in order to select, in each image selection iteration loop, one image that is related to the MGS|max having the greatest value among all the q MGS|max values.

FIG. 8 schematically illustrates an implementation of an image selection method according to an example embodiment. A human GI tract (schematically shown at 800) includes, among other things, a small bowel (SB) segment 810, and a colon 820 segment. An in-vivo device 830 similar to in-vivo device 40 may capture images in GI tract 800 while moving in direction 840.

Graph 850 is a time graph showing temporally ordered images in association with the part of GI tract from which the images were captured. For example, the first image that was captured in the SB (810) is image 812, which was captured at time t1, and the last image captured in the SB (810) is image 814, and it was captured at time t2 ($t2>t1$). Similarly, the first image that was captured in the colon (810) is image 822, which was captured at time t3, and the last image captured in the colon (810) is image 824, and it was captured at time t4 ($t4>t3>t2>t1$). According to graph 850 images were captured using a constant imaging rate. However, the imaging rate may vary, for example according to changes in the movement of the in-vivo device, or according to changes in the remaining battery power, etc., and the image selection methods disclosed herein may, as well, apply to embodiments where the imaging rate varies.

Assuming that the user (e.g., a physician) wants to select only images that originate from a particular segment of GI tract 800, the user may indicate this to a workstation (e.g., workstation 13), for example by mouse-clicking a dedicated input box on a computer display (e.g., display 18), and a data processor (e.g., data processor 14), complying with the user's input, may exclude all extraneous parts of the GI tract (800) from consideration by zeroing out all general scores that are related to the extraneous GI parts. For example (referring to graph 860), it is assumed that the user inputs to the workstation (for the data processor) an instruction to select only those 'pathological' images that originate from the small bowel (810). In response to the user's instruction, the data processor may zero out the general scores (GSs) related to the images that precede the images of the small bowel as shown at 862 (image numbers 123-124), and also the general scores related to the images that follow the images of the small bowel, as shown at 864 (image numbers 150-163). By zeroing out (e.g., set to zero) the general scores related to the images to be excluded, the images ultimately selected by the data processor originate only from the small bowel. ('Preceding a particular image' and 'following a particular image' respectively mean an image captured before the particular image, and an image captured after the particular image.)

An image may be noisy, for example, in the sense that it contains bubbles and/or gastric content and/or if the image provides tissue coverage below a tissue coverage threshold value and/or if the image complies with a darkness criterion, etc. In such cases, it may be beneficial to exclude such images from the image selection process. To that effect, the image selection process may additionally include, for example, a bubble detector and/or a gastric content detector and/or a tissue coverage detector, etc., to detect such images, and the methods described herein may include zeroing out (e.g., setting to zero) a general score of an image if the image is noisy. By way of example, image numbers 132 and 139 are example images containing bubbles and gastric content, so the general scores related to them are respectively shown zeroed out at 866 and 868.

In another example (referring to graph 870), it is assumed that the user inputs to the workstation (for the data processor) an instruction to select only images that originate from the colon (820). In response to the user's instruction, the data processor may zero out the general scores related to the images preceding the images of the colon, as shown at 872 (image numbers 123-149), and also the general scores related to the images that follow the images of the small bowel, as shown at 874 (image numbers 162-163). By zeroing out the general scores related to the images that are to be excluded from the image selection process, the images ultimately selected by the data processor originate only from the colon.

After the images related to the extraneous segments of GI tract 800 are excluded from the image selection process (e.g., by zeroing out their general scores), the non-excluded images (the remaining images that are captured in the GI's segment of interest) may be partitioned into image subgroups, then, in each image subgroup an MGS (or MGSs) may be identified, and, then, the MGSs of the image subgroups may be processed in order to select images from the GI segment of interest (e.g., small bowel segment 810, or colon 820, or any other segment of GI tract 800).

In some embodiments that are described herein, for example in connection with FIG. 6A, the GSs of images that are near a selected image are variably suppressed (e.g., their value is lowered), thus still giving the near images a chance to be selected as well. "Typically, the number of images that are near a selected image and contain the same object is known only post factum, that is, after the tracking process, which searches for a certain object in the near images, is completed for the related selected image. (A tracking process may be regarded as completed after the last image containing a same object as in the selected image is found by the processor performing the tracking process. (The object contained in a selected image is referred to herein as 'original object'.) That is, the processor may in an orderly manner 'pervade' the tracking process from a selected image to one image after another (in both directions) as long as it finds the original object in these images, and it may terminate the tracking process when a next image does not contain the original object.) In addition, if many images on one side (within the ordering in the image stream) or on two sides of a selected image contain the original object, such images may be relatively chronologically remote from the selected image (e.g., 50 images away from the selected image, 45 images ahead of the selected image, etc.) and such images may still be regarded as 'near' images. (A remote image may still be regarded as a near image if the tracking process indicates that the remote image, and all the images intervening between the remote image and the selected image, all contain the same object.) Using this embodiment may, therefore, result in redundant selection of additional image(s) that contain (show) a same object (e.g., pathology), for example a same polyp, a same lesion, etc. However, in some cases it may be desired to ensure that only one image that shows a particular object (e.g., pathology) be selected in order to avoid selecting redundant images and, in general, to better use a given (e.g., predetermined) image budget. Using the embodiment shown in FIG. 9 may ensure that only one image is selected for each object (e.g., for each particular pathology). After a particular image is selected for display, or for another purpose, the images near the selected image may still be made available to a user (e.g., physician), which may, if desired, also select these images, for example for review (e.g., as a video clip, as a 'collage', etc.), or for a processor, for example to manipulate the entire image subgroup related to the selected image.

Using image characteristics as an object may enable defining multiple image subgroups first and, then, to select images by manipulating their general scores, for example in the way described in connection with FIGS. 6A-6B and FIG. 7. Using imaged objects as an object, as described, for example, in connection with FIG. 9, may enable selecting an image first, and, then, to use the selected image to define 'its' subgroup in order to nullify its entire subgroup before a next image is selected, and so on. Regardless of whether a subgroup of images is found first and then an image is, or may be, selected from that subgroup, or whether an image is selected first and then its subgroup is formed, the general scores (GSs) of each subgroup are manipulated (e.g., nullified or modified) before a next image is selected.

Figure 9:
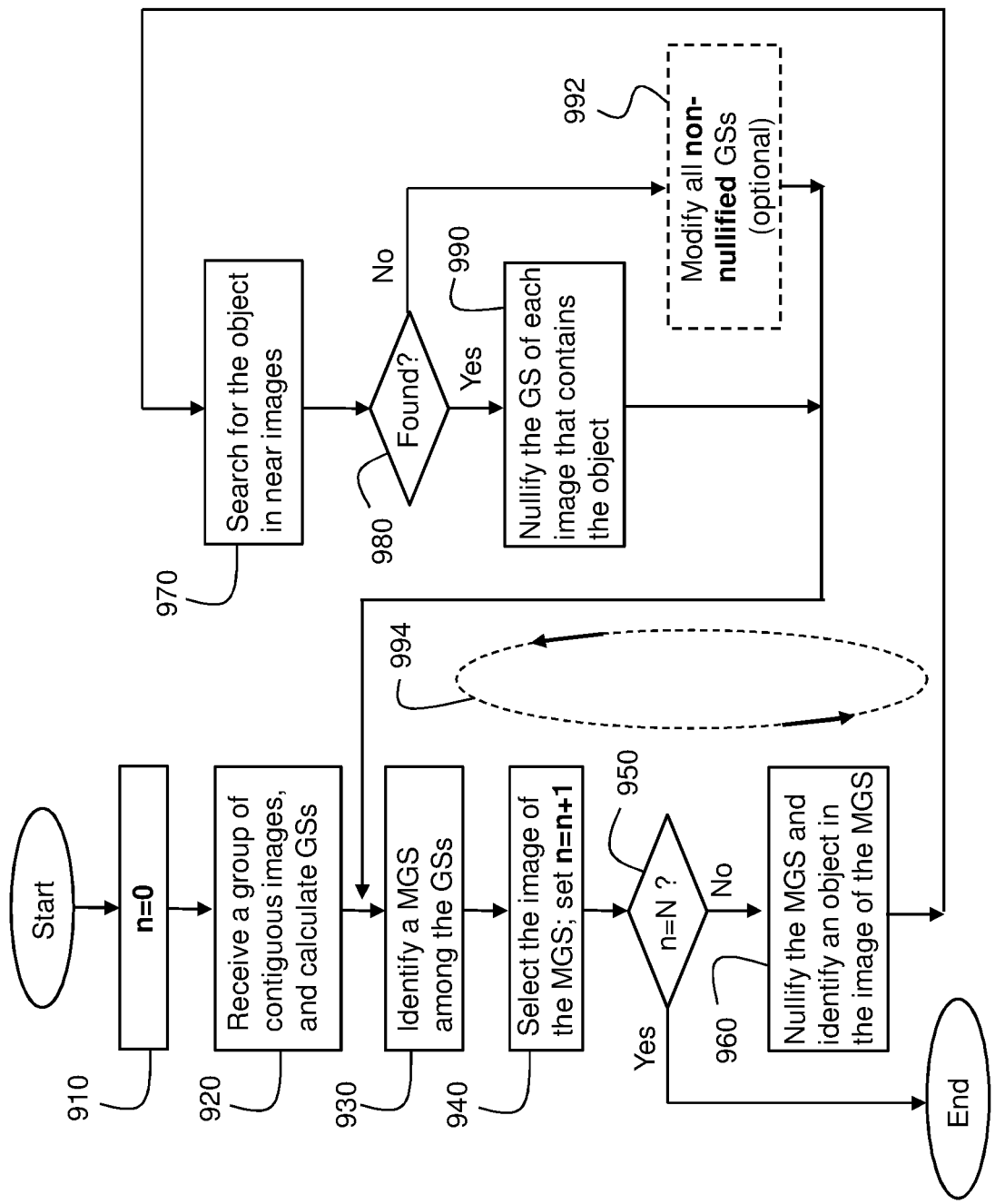
FIG. 9 shows a method for selecting images originating from one imager according to another example embodiment of the invention.

FIG. 9 shows a method of selecting images for display (or for any other purpose) according to another example embodiment of the invention. At step 910 the value of a loop index n is initially set to zero (n=0). At step 920 a processor may receive, or retrieve, a group (a series) of consecutive images that originate from a GI tract of a subject and may calculate a general score (GS) for each image. The processor may use any of the methods described herein or other methods to calculate the general scores (GSs) for the images.

At step 930, the processor may identify the greatest GS (a MGS)) among the GSs, and, at step 940 the processor may select (or mark), for example for display, the image whose GS is the MGS, and set the value of n to 1 (n=n+1=1) to indicate that, at this stage, one image has been selected.

At step 950, the processor may check whether the value of n is equal to N (N being any preferred maximum number of images that is allowed to be selected; e.g., N=10, 25, 100, etc.) If the number of images that were already selected is equal to N (this condition is shown as "Yes" at step 950), the images selection process is terminated. However, if the number of images that were already selected is (still) lower than N (this condition is shown as "No" at step 950), at step 960 processor nullifies (e.g., sets to zero) the value the MGS of (related to) the selected image, and, in addition, the processor may identify an object of clinical importance (e.g., polyp) in the selected image. (It is assumed with high level of confidence that an image includes such an object because its GS is currently the greatest.)

At step 970, the processor may search for the same object of clinical importance (the object that is the same as or identical to the object that has been identified in the selected image) in images that are near the currently selected image. For example, the processor may apply a tracking mechanism to try to identify near images, on both sides of the selected image (preceding images and subsequent images), which contain a same object (e.g., a same pathology) for which the selected image was probably selected.

If the processor finds images near the currently selected image which contain the same object as in the currently selected image (this condition is shown as "Yes" at step 980), then, at step 990, the processor nullifies the GS of each image that contains the object. Nullifying the GSs of all the near images (images near the currently selected image) excludes the near images from the images selection process, thus ensuring that the object identified (detected) in the selected image will be shown (or selected for any other reason; e.g., for further processing) only once, that is, by only one, representative, image. However, if the processor does not find images 'near' the currently selected image which contain the same object as in the currently selected image (this condition is shown as "No" at step 980), then, at step 992, the processor may modify all the GSs that have not yet been nullified. The rationale behind modifying the non-nullified GSs at step 992 is that if an image near the currently selected image does not contain the object for which the currently selected imager was selected, the image near the selected image (the 'near image') may contain another object that may warrant selection of this image. Therefore, the GSs of the near images may be modified (not nullified) in order to give them, or to some of them, a chance to be selected as well. Modifying the non-nullified GSs at step 992 may be implemented by using any modification method that is described herein, or any other suitable modification method. Step 992 (modifying non-nullified GSs) may be optional. That is, the processor executing the embodiment of FIG. 9 may skip step 992 and proceed to step 930 in order to commence another iteration or repetition 994. In other words, in some embodiments the processor may not modify general scores but, rather, identify another (a next) greatest GS, select the related image, nullify its 'neighboring' (near) GSs (if there are near images that contain the same object as the related selected image), then, again (at step 930), identify the next currently greatest GS among the non-nullified GSs, and so on (proceeding with steps 940, 950, and so on).

At each iteration or repetition (994) step 970 may result in a subgroup of images that includes a selected image, as a base image, and images that are near the base image and include the same object. An image subgroup may sometimes include one image, which is the selected image, or a plurality of images.

After images that contain the same object as the currently selected image are nullified (per step 990), or after all non-nullified GSs are modified (if step 992 is not skipped by the processor), another iteration, or loop repetition 994 may commence, at step 930, in order to select another image. That is, at step 930 the processor may identify the current (a new) greatest GS (a current/new MGS) among the GSs. or among the modified GSs, then select, at step 940, the image related to the MGS, then at step 960, nullify the current MGS and identify a new object (an object that is different than the object contained in the previously selected image(s), then, at step 970, search for the same new object in images that are near the newly selected image, and so on.

An image that includes a same object as in a selected image does not necessarily mean that the object is in the same location or has a same orientation in these images. For example, a same object may be displaced between adjacent images, and/or the object in one image may be rotated relative to the object image in the adjacent image. The processor may use any known image processing method to determine whether two images show, or contain, a same object (e.g., a same polyp). Such techniques are well known in the art.

Figure 10A:
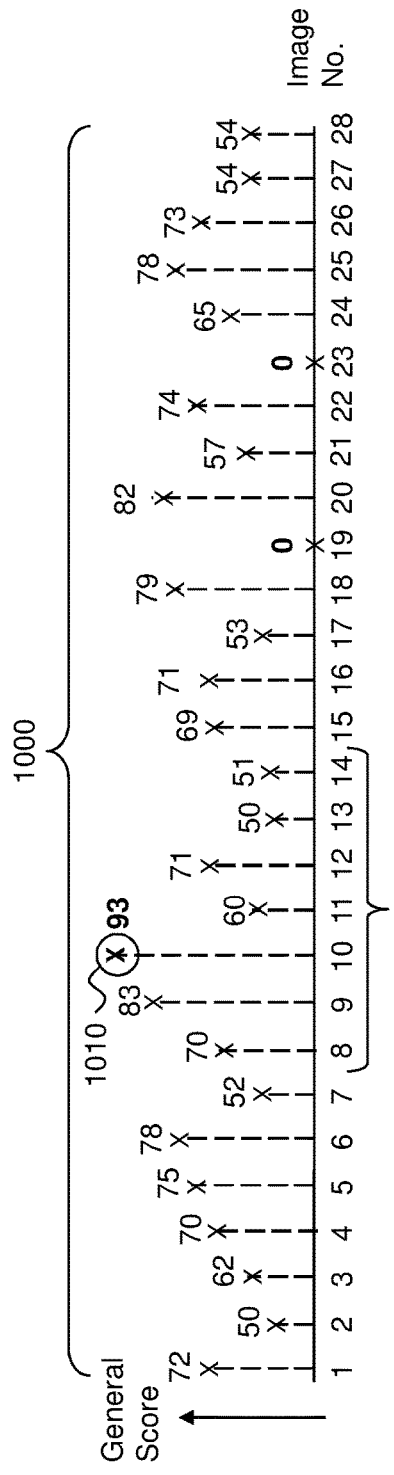
FIGS. 10A-10C demonstrate a scores modification process in accordance with the embodiment shown in FIG. 9.
Figure 10B:
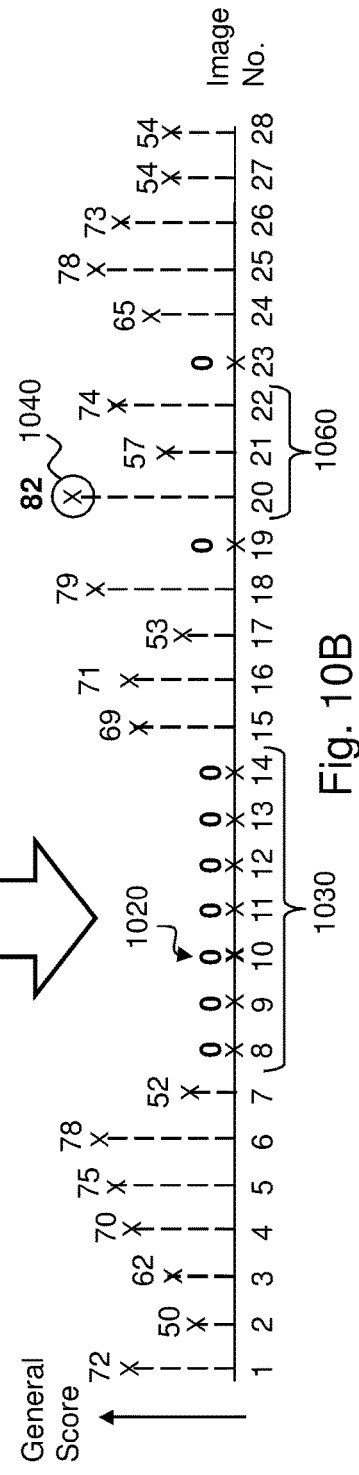
Figure 10C:
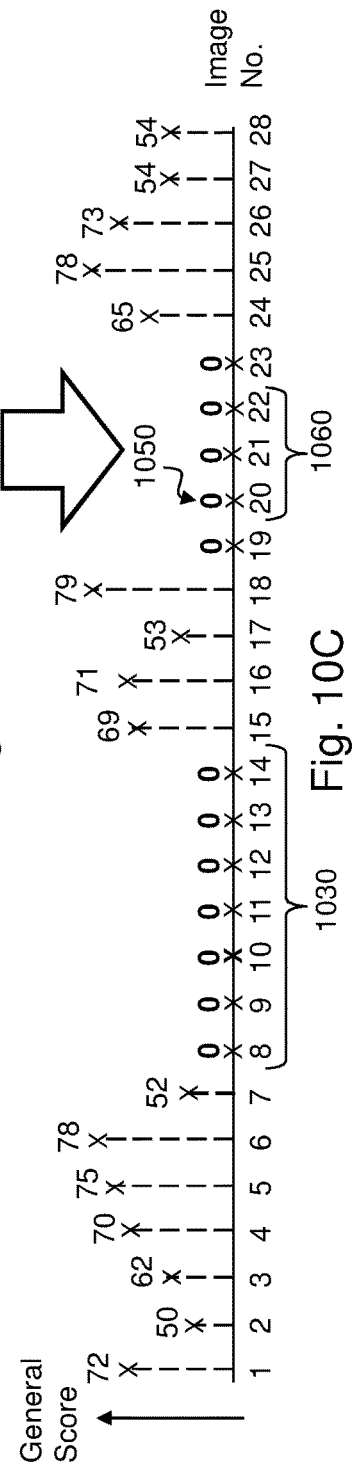

FIGS. 10A-10C demonstrate an image selection process in accordance with an example embodiment. FIG. 10A shows an example image group 1000 including twenty eight contiguous images captured by an in-vivo device including one imager, and their respective general scores (GSs). (The 28 images are shown ordered temporally, according to the time of their capture, with image number '1' captured first and image number '28' captured last.) In practice, the number of images in an image group may be very large (e.g., tens of thousands), however, as in the other drawings, the small number of images shown in FIG. 10A is used only for illustrative purpose.

FIG. 10A will be described in association with FIG. 9. After a general score is calculated for the twenty eight images, for example by a processor, (per step 920), the processor may identify the currently greatest GS (a current MGS), at step 930. Referring to FIG. 10A, the currently (at this stage the first) greatest GS, or MGS, is the GS of image number ten. (The value of the GS for image number '10' is 93, as shown at 1010.) Therefore, the processor selects (per step 940) image number '10' because it is related to the current MGS. Assume that it is wanted to select more images (e.g., 35 images). Accordingly, the processor proceeds the images selection process by nullifying, at step 960, the MGS (e.g., by setting its value to zero, as shown at 1020 in FIG. 10B), and by identifying an object in the selected image (also at step 960).

Then, at step 970 the processor searches for the same object in images which are near the selected image. Referring to FIG. 10A, assume that, by way of example, images numbers '8' and '9' (two images that precede image number '10', the currently selected image) and images numbers '11', '12', '13' and '14' (four images subsequent to image number '10') contain the same object as image number '10'. (In other words, all the images that make up or form image group 1030 contain the same object.) Therefore, at step 990, the processor nullifies the GSs of all the images in image group 1030, due to all of them containing the same object, so only one, representative, image should be selected. The nullified values of these GSs are shown in FIG. 10B. For example, while the value of the GS of image number '8' is 70 (in FIG. 10A), its value in FIG. 10B (that is, after nullifying it in step 990) is zero. Nullifying the GSs of image number '10' and the GSs of the images near image number '10' excludes the entire image subgroup 1030 from the image selection process, except for image number '10', which is selected as a representative image of this image subgroup because, at this stage (at this algorithm repetition), it has the greatest GS.

After the first image group (image group 1030) is excluded from the image selection process, the processor identifies, again at step 930, the next MGS, which has, in the example of FIG. 10B, the value 82 (this GS was calculated for image number '20' and is shown at 1040). As with the previous MGS, the processor selects image number '20' at step 940, and nullifies the value of its GS at step 960. The nullified MGS value 1040 of image number '20' (the second selected image) is shown at 1050. By way of example, assume that only two images (image numbers '21' and '22') that are near the currently selected image (image number '20') include a same object as image number '20'. Therefore, the entire image subgroup 1060 is excluded from the image selection process—image number '20' for already being selected due to its GS being the second greatest GS, and image numbers '21'-'22' due to them containing a same object as image number '20'.

FIGS. 10A-10C demonstrate that, with each iteration or repetition 994 of the embodiment of FIG. 9, another subgroup of images may be detracted or removed from the image selection process. A third iteration or repetition 944 (FIG. 9) may be applied to the remaining GSs in FIG. 10C; e.g., to the GSs remaining after the exclusion of image subgroups 1030 and 1060. If a selected image does not have any near image that includes the same object, the next image may be selected in a similar way without modifying the non-nullified GSs (by skipping or ignoring step 992), or by modifying the non-nullified GSs, per step 992.

The image selection methods disclosed herein may be implemented in various ways, for example by using various score modification mechanisms. For example, the modification function used to modify scores may be selected from a group consisting of: symmetrical function or asymmetrical function ('symmetrical' and 'asymmetrical' are with respect to already selected image(s)), linear function, non-linear. Gaussian exponent, exponent with an absolute value of distance, a step function, and a triangularly shaped function with its apex located at a selected image and linearly decreases as a function of distance. The modification function may be selected according to a parameter selected from a group consisting of: the type of pathology, location in the GI tract and velocity of the in-vivo device in the body lumen. For example, the image selection process may be applied to all the images captured by the in-vivo device, and the process may include application of the same modification function to the related MGSs; the image selection process may be applied to all the images captured by the in-vivo device, but the process may include application of different modification functions to MGSs that are related to images captured in different portions, or segments, of the body lumen; the image selection process may be applied only to images captured by the in-vivo device in a particular portion or segment of the body lumen, and the process may include application of the same modification function to the related MGSs, or different modification functions; a modification function may be speed-dependent in the sense that when the in-vivo device moves in the GI tract at a low speed, suppression may be applied only to, or more rigorously to, MGSs that are related to images which are relatively close to a selected image, and when the in-vivo device moves in the GI tract at a high speed, suppression may be applied only, or more rigorously, to MGSs that are related to images which are relatively far from a selected image; when the in-vivo device produces, for example, two series of images (one for each imager), if one imager takes a picture of a pathology (e.g., polyp), images from the other imager, which are close in time to that image may be suppressed significantly because there is no point in selecting additional images of the same pathology. (Images of the same pathology may be taken, for example, when the in-vivo device moves slowly, or when the images capturing rate is high comparing to the movement of the in-vivo device, and/or when the two (or more) imagers of the in-vivo device take a picture of the same pathology.)

In some embodiments. MGSs that are calculated for images related to one image group may be suppressed also with respect to images that are related to MGSs calculated for images that are related to another image group. For example, if there are two imagers, one imager may be looking in a forward direction (a direction of movement of the in-vivo device) and the other imager may be looking backward (in the opposite direction). Images captured by both imagers may be 'registered' between consecutive images in order to determine which imager is 'zooming in' and which one is zooming out. Then, an unsymmetrical modification function may reject images taken in the same GI site by the other head.

While, data gathering, storage and processing are performed by certain units, the system and method of the present invention may be practiced with alternate configurations. For example, the components gathering and transmitting image data need not be contained in a capsule, but may be contained in any other device that is suitable for traversing a lumen in a human body, such as an endoscope, stent, catheter, needle, etc.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

The invention claimed is:

1. A method for selecting images for processing from images captured by an in-vivo device, the method comprising: for a group of contiguous images captured in a body lumen, with each image is associated a general score, GS, indicative of a probability that the image includes at least one type of pathology, performing using a processor,
(i) identifying a greatest GS among the GSs, selecting an image related to the greatest GS and nullifying the greatest GS related to the selected image;
(ii) identifying an object in the selected image;
(iii) searching for an object which is the same as the identified object in images near the selected image; and
(iv) nullifying the GSs related to the images near the selected image;
repeating steps (i)-(iv), for the non-nullified GSs, until a number N of images is selected, or until the value of an identified greatest GS is lower than a score threshold; and
displaying the N selected images or a subset of the N selected images.

2. The method as in claim 1, wherein the object in the selected image is selected from the group consisting of: (1) an entire image, the method comprising determining that the selected image and images near the selected image make up an image subgroup if there is similarity between these images, and (2) a pathology, the method comprising determining that the selected image and images near the selected image make up an image subgroup if these images include a same pathology.

3. The method as in claim 1, wherein the step of searching for the same object in images near the selected image comprises tracking the object backward, in images preceding the selected image, and tracking the object forward, in images subsequent to the selected image.

4. The method as in claim 1, comprising modifying non-nullified GSs based on a distance d between each image related to a non-nullified GS and a nearest selected image.

5. The method as in claim 4, wherein modifying a particular GS comprises identifying a minimum distance, Dmin, between the image related to the particular GS and any of the selected images, and modifying the particular GS using the minimum distance, Dmin.

6. The method as in claim 5, wherein the smaller Dmin, the greater a reduction in the value of the particular GS.

7. The method as in claim 4, wherein the distance d between an image related to a GS and a selected image is calculated or measured in units of: (i) time, or (ii) a number of intervening images, or (iii) a number of intervening image subgroups, or (iv) a distance that the in-vivo device traveled in the body lumen while taking the images, or (v) a distance that the in-vivo device traveled in the body lumen with respect to a landmark in the group of images or in the body lumen, or (vi) a percentage of a video clip including all, or most of, the group of contiguous images.

8. The method as in claim 7, wherein each unit instance is calculated or measured as:
(i) an absolute value calculated or measured relative to a beginning of the group of contiguous images, or relative to a beginning of the body lumen, or relative to a landmark in the group of contiguous images or in the body lumen, or as (ii) a percentage or fraction of the group of contiguous images or body lumen, or (iii) a percentage or fraction of a video clip including all, or most of, the group of contiguous images, or (iv) a percentage or fraction of a distance travelled by the in-vivo device, or (v) a percentage or fraction of a time travelled by the in-vivo device.

9. The method as in claim 4, wherein modifying GSs comprises applying a modification function to GSs with respect to a selected image.

10. The method as in claim 4, comprising applying a modification function to GSs based on a location in the body lumen at which the images related to the GSs were captured.

11. The method as in claim 10, wherein the body lumen is the gastrointestinal tract, the method comprising applying a first modification function to GSs related to images captured in the small bowel, and applying a second modification function to GSs related to images captured in the colon.

12. The method as in claim 10, wherein the modification function is selected according to a parameter selected from the group consisting of: type of pathology, location of the in-vivo device in the GI tract and velocity of the in-vivo device in the body lumen.

13. The method as in claim 1, wherein the body lumen is the gastrointestinal tract, comprising zeroing out a GS of an image if the image is noisy, wherein an image is regarded as noisy if the image contains bubbles and/or gastric content, and/or if the image provides tissue coverage below a tissue coverage threshold value, and/or the image complies with a darkness criterion.

14. The method as in claim 1, wherein a GS associated with an image is calculated using a number in of score values, S1, . . . Sm, that are respectively output by m pathology detectors, the m score values indicating probabilities that the image includes m, or k (k<m), types of pathologies.

15. The method as in claim 1, wherein a pathology is selected from the group consisting of: a polyp, a bleeding, a diverticulum, an ulcer, a lesion and a red pathology.

16. A system for selecting images from captured y an in-vivo device, the system comprising:
a storage unit; and
a processor to:
for a group of contiguous images captured in a body lumen, with each image is associated a general score, GS, indicative of a probability that the image includes at least one type of pathology, perform:
(i) dividing a portion of the group of contiguous images into image subgroups, each image subgroup comprising a base image and images resembling the base image;
(ii) identifying a maximum general score ("MGS") for each image subgroup;
(iii) selecting an image associated with a greatest MGS (MGS|max) among the MGSs, and nullifying the greatest MGS related to the selected image;
(iv) modifying each particular MGS based on a distance d between an image related to the particular MGS and a nearest selected image;
(v) identifying a modified greatest general score (MSG-|max) from the modified MGSs;
repeating steps (iii)-(v) until a predetermined criterion selected from the group consisting of a predetermined number N of images is selected and a score threshold is met; and
displaying the N selected images or a subset of the N selected images.

17. The system as in claim 16, wherein modifying general scores (GSs) comprises applying a modification function to the GSs with respect to a selected image.

18. The system as in claim 17, wherein the modification function is selected according to a parameter selected from the group consisting of: a location in the body lumen at which the images related to the GSs were captured, a type of pathology, and velocity of the in-vivo device in the body lumen.

19. A method for selecting images from images captured by a number q of imagers of an in-vivo device, the method comprising, using a processor:

for q groups of contiguous images respectively captured in a body lumen by q imagers, with each image of each group are associated: a general score (GS) indicative of a probability that the image includes at least one type of pathology, and a distance d, d, indicative of a distance between images of the respective group, performing, for each image group of the q groups of contiguous images, performing:
  (A) dividing, or separating, the image group, or a portion thereof, into image subgroups, each image subgroup comprising a base image and images resembling to the base image, and
  (B) identifying a set Set(i) (i=1, 2, 3, ...) of maximum general scores (MGSs), the set Set(i) of maximum general scores comprising a maximum general score (MGS) for each image subgroup of the image group;

selecting images for processing, the selecting comprising:
  (i) identifying a maximum MGS (MGS|max) in each set S(i) of MGSs;
  (ii) identifying, among all the MGSs|max, the greatest MGS|max, and selecting the image related to the greatest MGS|max;
  (iii) nullifying the greatest MGS|max related to the selected image;
  (iv) modifying the particular set Set(i) of MGSs related to the selected image based on a distance d between images respectively related to the MGSs of the particular set Set(i) of MGSs and each selected image;

repeating steps (i)-(iv) until a predetermined criterion selected from a group consisting of a number N of images and a score threshold is met; and displaying the N images or a subset of the N images.

20. The method as in claim 19, wherein the in-vivo device comprises a number of imagers selected from one and two.

21. The method as in claim 19, wherein modifying a particular set Set(i) of MGSs related to a selected image originating from a first imager comprises modifying MGSs of the particular set Set(i) also based on images originating from the second imager.

* * * * *